US012633377B2

(12) United States Patent
Xu et al.

(10) Patent No.: US 12,633,377 B2
(45) Date of Patent: May 19, 2026

(54) METHODS FOR DETECTING VARIANTS IN NEXT-GENERATION SEQUENCING GENOMIC DATA

(71) Applicant: SOPHIA GENETICS SA, Saint-Sulpice (CH)

(72) Inventors: Zhenyu Xu, Saint-Sulpice (CH); Lin Song, Saint-Sulpice (CH)

(73) Assignee: Sophia Genetics S.A., Rolle (CH)

( * ) Notice: Subject to any disclaimer, the term of this patent is extended or adjusted under 35 U.S.C. 154(b) by 541 days.

(21) Appl. No.: 17/251,293

(22) PCT Filed: Jun. 14, 2019

(86) PCT No.: PCT/EP2019/065777
§ 371 (c)(1),
(2) Date: Dec. 11, 2020

(87) PCT Pub. No.: WO2019/238963
PCT Pub. Date: Dec. 19, 2019

(65) Prior Publication Data
US 2021/0125689 A1      Apr. 29, 2021

(30) Foreign Application Priority Data
Jun. 14, 2018    (EP) ..................................... 18177876

(51) Int. Cl.
*G16B 30/10*          (2019.01)
*G16B 5/20*           (2019.01)
(52) U.S. Cl.
CPC ............... *G16B 30/10* (2019.02); *G16B 5/20* (2019.02)
(58) Field of Classification Search
None
See application file for complete search history.

(56) References Cited

U.S. PATENT DOCUMENTS

2009/0026082 A1      1/2009  Rothberg et al.
2014/0052381 A1*     2/2014  Utiramerur ............ G16B 30/00
                                                      702/19

FOREIGN PATENT DOCUMENTS

WO      WO-2016009224 A1 *  1/2016  ........... C12Q 1/6827
WO          2018/104466 A1     6/2018

OTHER PUBLICATIONS

Heard, Nicholas A. "Iterative Reclassification in Agglomerative Clustering." Journal of Computational and Graphical Statistics, vol. 20, No. 4, 2011, pp. 920-936. (Year: 2011).*
(Continued)

*Primary Examiner* — Karlheinz R. Skowronek
*Assistant Examiner* — Mary C Leverett
(74) *Attorney, Agent, or Firm* — Bochner PLLC; Andrew D. Bochner; Caitlin A. Hyland

(57) ABSTRACT

A genomic data analyzer may be configured to detect and characterize, with a variant calling module, genomic variants from next generation sequencing reads out of a pool of enriched genomic patient samples without suffering from next generation sequencing workflow biases such as those introduced by sequencing errors in particular in repeat patterns regions of the human genome such as homopolymers or heteropolymers. The variant calling module may estimate the probability distribution of the length of the repeat pattern for each patient sample and cross-analyze it against other samples in a single experimental pool to identify best-fit variant models for each pair of samples. The variant calling module may further group samples according to their matching best-fit variant models and identify which group of patient samples carries the wild type reference without the need for control data in the pool. The variant calling module may subsequently characterize the homozygous or heterozygous repeat patterns variants for each
(Continued)

patient sample with improved specificity and accuracy even in the presence of next generation sequencing biases.

20 Claims, 23 Drawing Sheets

(56) References Cited

OTHER PUBLICATIONS

Min Zhao et al. Computational tools for copy number variation (CNV) detection using next-generation sequencing data: features and perspectives. BMC Bioinformatics 2013, 14(Suppl 11):S1 (Year: 2013).*

Treangen, Todd & Salzberg, Steven. (2011). Repetitive DNA and next-generation sequencing: Computational challenges and solutions. Nature reviews. Genetics. 13. 36-46. (Year: 2012).*

Feng, Weixing er al. (2016). Improving alignment accuracy on homopolymer regions for semiconductor-based sequencing technologies. BMC Genomics. 17. (Year: 2016).*

Duan J, Deng HW, Wang YP. Common copy number variation detection from multiple sequenced samples. IEEE Trans Biomed Eng. Mar. 2014;61(3):928-37. (Year: 2014).*

Poulet et al., "Improved Efficiency and Reliability of NGS Amplicon Sequencing Data Analysis for Genetic Diagnostic Procedures Using AGSA Software", Biomed Research International, vol. 2016, XP055620816, ISSN: 2314-6133, DOI: 10.1155/ 2016/5623089, Jan. 1, 2016, pp. 1-11.

International Search Report, mailed Oct. 1, 2019 by the European Patent Office 9EPO), in International Application No. PCT/EP2019/065777.

Written Opinion of the International Searching Authority, mailed Oct. 1, 2019 by the European Patent Office (EPO), in International Application No. PCT/EP2019/065777.

* cited by examiner with experiment error

| homopoly mer length | -3 | -2 | -1 | 0 | +1 | +2 | +3 |
|---|---|---|---|---|---|---|---|
| fraction | 0 | 0.1 | 0.2 | 0.6 | 0.1 | 0 | 0 |

↓ split to 2 alleles

| | -3 | -2 | -1 | 0 | +1 | +2 | +3 |
|---|---|---|---|---|---|---|---|
| allele 1 | 0 | 0.05 | 0.1 | 0.3 | 0.05 | 0 | 0 |
| allele 2 | 0 | 0.05 | 0.1 | 0.3 | 0.05 | 0 | 0 |

↓ mutation

| | -3 | -2 | -1 | 0 | +1 | +2 | +3 |
|---|---|---|---|---|---|---|---|
| allele 1 | 0.05 | 0.1 | 0.3 | 0.05 | 0 | 0 | 0 |
| allele 2 | 0 | 0.05 | 0.1 | 0.3 | 0.05 | 0 | 0 |

↓ merge 2 alleles

| | -3 | -2 | -1 | 0 | +1 | +2 | +3 |
|---|---|---|---|---|---|---|---|
| fraction | 0.05 | 0.15 | 0.4 | 0.35 | 0.05 | 0 | 0 |

|    | S2         | S3         | S4         | S5         | S6          | S7         | S8         |
|----|------------|------------|------------|------------|-------------|------------|------------|
| S1 | 0/0 0.46   | 0/0 0.60   | 0/0 0.67   | 0/0 0.64   | 0/0 0.67    | 0/0 0.91   | 0/0 0.69   |
| S2 |            | 0/0 0.32   | -1/0 0.08  | -1/0 0.10  | NA/NA NA    | 0/0 0.18   | -1/0 0.10  |
| S3 |            |            | 0/0 0.12   | 0/0 0.29   | NA/NA NA    | 0/0 0.38   | 0/0 0.32   |
| S4 |            |            |            | 0/0 0.76   | 0/0 0.92    | 0/0 0.74   | 0/0 0.79   |
| S5 |            |            |            |            | 0/0 0.64    | 0/0 0.68   | 0/0 0.96   |
| S6 |            |            |            |            |             | 0/0 0.75   | 0/0 0.72   |
| S7 |            |            |            |            |             |            | 0/0 0.68   |

FIG.10

|  | S2 | S3 | S4 | S5 | S6 | S7 | S8 |
|---|---|---|---|---|---|---|---|
| S1 | 0/0 0.46 | 0/0 0.60 | 0/0 0.67 | 0/0 0.64 | 0/0 0.67 | 0/0 0.91 | 0/0 0.69 |
| S2 |  | 0/0 0.32 | -1/0 0.08 | -1/0 0.10 | NA/NA NA | 0/0 0.18 | -1/0 0.10 |
| S3 |  |  | 0/0 0.12 | 0/0 0.29 | NA/NA NA | 0/0 0.38 | 0/0 0.32 |
| S4 |  |  |  | 0/0 0.76 | 0/0 0.92 | 0/0 0.74 | 0/0 0.79 |
| S5 |  |  |  |  | 0/0 0.64 | 0/0 0.68 | 0/0 0.96 |
| S6 |  |  |  |  |  | 0/0 0.75 | 0/0 0.72 |
| S7 |  |  |  |  |  |  | 0/0 0.68 |

FIG.11

| | S2 | S3 | S4 | S5 | S6 | S7 | S8 |
|---|---|---|---|---|---|---|---|
| S1 | 0/0 0.46 | 0/0 0.60 | 0/0 0.67 | 0/0 0.64 | 0/0 0.67 | 0/0 0.91 | 0/0 0.69 |
| S2 | | 0/0 0.32 | -1/0 0.08 | -1/0 0.10 | NA/NA NA | 0/0 0.18 | -1/0 0.10 |
| S3 | | | 0/0 0.12 | 0/0 0.29 | NA/NA NA | 0/0 0.38 | 0/0 0.32 |
| S4 | | | | 0/0 0.76 | 0/0 0.92 | 0/0 0.74 | 0/0 0.79 |
| S5 | | | | | 0/0 0.64 | 0/0 0.68 | 0/0 0.96 |
| S6 | | | | | | 0/0 0.75 | 0/0 0.72 |
| S7 | | | | | | | 0/0 0.68 |

FIG.12

| | S2 | S3 | S4 | S5 | S6 | S7 | S8 | | | |
|---|---|---|---|---|---|---|---|---|---|---|
| | | | | | | | | .... | -1/0 0.50 | 0/0 0.32 |
| S1 | 0/0 0.13 | 0/0 1.00 | 0/0 0.69 | 0/0 0.71 | 0/0 1.00 | 0/0 1.00 | 0/0 0.72 | .... | 0/0 0.88 | 0/0 0.79 |
| S2 | | 0/0 0.13 | 0/0 0.13 | 0/0 0.13 | 0/0 0.12 | 0/0 0.12 | 0/0 0.12 | .... | 0/0 0.98 | 0/0 0.96 |
| S3 | | | 0/0 0.61 | 0/0 0.62 | 0/0 1.00 | 0/0 1.00 | 0/0 0.64 | .... | 0/0 0.94 | 0/0 0.72 |
| S4 | | | | 0/0 1.00 | 0/0 0.83 | 0/0 0.60 | 0/0 1.00 | .... | 0/0 0.98 | 0/0 0.68 |
| S5 | | | | | 0/0 0.84 | 0/0 0.62 | 0/0 1.00 | .... | 0/0 0.97 | |
| S6 | | | | | | 0/0 1.00 | 0/0 0.84 | .... | | |
| S7 | | | | | | | 0/0 0.63 | | | |

Stacked (upper) layers:

| | S2 | S3 | S4 | S5 | S6 | S7 | S8 | |
|---|---|---|---|---|---|---|---|---|
| | S2 | S3 | S4 | S5 | S6 | S7 | S8 | 0/0 0.69 |
| | S2 | S3 | S4 | S5 | S6 | S7 | S8 | 0/0 0.94 / -1/0 0.10 |

FIG.13

|    | S2   | S3  | S4  | S5  | S6  | S7  | S8  |
|----|------|-----|-----|-----|-----|-----|-----|
| S1 | -1/0 | 0/0 | 0/0 | 0/0 | 0/0 | 0/0 | 0/0 |
| S2 |      | 0/1 | 0/1 | 0/1 | 0/1 | 0/1 | 0/1 |
| S3 |      |     | 0/0 | 0/0 | 0/0 | 0/0 | 0/0 |
| S4 |      |     |     | 0/0 | 0/0 | 0/0 | 0/0 |
| S5 |      |     |     |     | 0/0 | 0/0 | 0/0 |
| S6 |      |     |     |     |     | 0/0 | 0/0 |
| S7 |      |     |     |     |     |     | 0/0 |

Group 1: {S1, S3, S4, S5, S6, S7, S8}
Group 2: {S2}

FIG.14

METHODS FOR DETECTING VARIANTS IN NEXT-GENERATION SEQUENCING GENOMIC DATA

FIELD OF THE INVENTION

Methods described herein relate to genomic analysis in general, and more specifically to next generation sequencing applications.

BACKGROUND OF THE INVENTION

Next-Generation Sequencing

High throughput next-generation sequencing (NGS) or massively parallel sequencing (MPS) technologies have significantly decreased the cost of DNA sequencing in the past decade. NGS has broad application in biology and dramatically changed the way of research or diagnosis methodologies. For example, RNA expression profiling or DNA sequencing can only be conducted with a few numbers of genes with traditional methods, such as quantitative PCR or Sanger sequencing. Even with microarrays, profiling the gene expression or identifying the mutation at the whole genome level can only be implemented for organisms whose genome size is relatively small. With NGS technology, RNA profiling or whole genome sequencing has become a routine practice now in biological research. On the other hand, due to the high throughput of NGS, multiplexed methods have been developed not just to sequence more regions but also to sequence more samples. Compared to the traditional Sanger sequencing technology, NGS enables the detection of mutation for much more samples in different genes in parallel. Due to its superiorities over traditional sequencing method, NGS sequencers are now replacing Sanger in routine diagnosis. In particular, genomic variations of individuals (germline) or of cancerous tissues (somatic) can now be routinely analyzed for a number of medical applications ranging from genetic disease diagnostic to pharmacogenomics fine-tuning of medication in precision medicine practice. NGS consists in processing multiple fragmented DNA sequence reads, typically short ones (less than 300 nucleotide base pairs). The resulting reads can then be compared to a reference genome by means of a number of bioinformatics methods, to identify small variants such as Single Nucleotide Polymorphisms (SNP) corresponding to a single nucleotide substitution, as well as short insertions and deletions (INDEL) of nucleotides in the DNA sequence compared to its reference.

Targeted Enrichment

In some pathologies, a specific gene variant has been associated with the illness, such as the BRCA1 and BRCA2 genes in certain forms of hereditary breast and ovarian cancers or the CFTR gene in cystic fibrosis. Rather than sequencing the whole genome (WGS) from an individual sample, the genomic analysis can focus on the genome region associated with the illness, by targeting, with a set of region-specific DNA primers or probes, and enriching or amplifying, for instance with PCR (Polymerase Chain Reaction), the biological DNA sample specifically for sub-regions corresponding to the gene along the DNA strand. A number of next generation sequencing assays have now been developed along those principles as ready-to-use biological kits, such as for instance the Multiplicom MASTR™ or the Illumina TruSeq® Amplicon assay kits to facilitate DNA based diagnostics with next generation sequencers, such as for instance the Illumina MiSeq® sequencer, in medical research and clinical practice.

Target enrichment may be achieved from a small sample of DNA by means of probe-based hybridization (on arrays or in-solution) or highly multiplexed PCR-based targeted exon enrichment, so that both the gene coverage/read depth and the amplification specificity (amplifying the right region, as measured by further alignment to the desired target regions) are maximized. Examples of commercially available target enrichment systems include Agilent SureSelect™ Target Enrichment System, Roche NimbleGen SeqCap EZ, Illumina Nextera Rapid Capture, Agilent Haploplex™, and Multiplicom MASTR™.

In order to maximize the use of the massively-parallel processing NGS sequencer, a number of samples are multiplexed in the targeted NGS experiment a pool of 48 or more target enrichment samples can thus be simultaneously input to the Illumina MiSeq sequencer for instance. Raw sequencing data out of the NGS sequencer may then be analyzed to identify specific subsequences, for instance by alignment to a reference genome. As a result, the amplification may produce more than a thousand reads for a given amplicon in a patient sample.

Next Generation Sequencing Workflow Automation

Next Generation Sequencing (NGS) enables in particular to detect and report small changes in the DNA sequence, such as single nucleotide polymorphisms (SNPs), insertions or deletions (INDELs), as compared to the reference genome, through bioinformatics methods such as sequencing read alignment, variant calling, and variant annotation. NGS workflows refer to the configuration and combination of such methods into an end-to-end genomic analysis application. In genomic research practice, NGS workflows are often manually setup and optimized using for instance dedicated scripts on a UNIX operating system, dedicated platforms including a graphical pipeline representation such as the Galaxy project, and/or a combination thereof. As clinical practice develops, NGS workflows may no longer be experimentally setup on a case-per-case basis, but rather integrated in SaaS (Software as a Service), PaaS (Platform as a Service) or IaaS (Infrastructure as a Service) offerings by third party providers. In that context, further automation of the NGS workflows is key to facilitate the routine integration of those services into the clinical practice.

Next Generation Sequencing Workflow Optimization

While next generation sequencing methods have been shown more efficient than traditional Sanger sequencing in the detection of SNPs and INDELs, their specificity (rate of true positive detection for a given genomic variant) and sensitivity (rate of true negative exclusion for a given genomic variant) may still be further improved in clinical practice. The specificity and sensitivity of NGS genomic analysis may be affected by a number of factors:

Biases introduced by the sequencing technology, for instance due to:

Length of the reads relative to the length of the fragments;

Too small number of reads (read depth);

Errors or low quality bases introduced during sequencing;

Inherent difficulties in counting homopolymer stretches, in particular with pyrosequencing (as in Roche 454 platforms) or semiconductor sequencing (as in Ion Torrent platforms, as described for instance by Rothberg in US patent application 2009/0026082), resulting in insertion and deletion errors;

Biases introduced by the DNA enrichment technology, for instance due to:

Primers or probes non specific binding, for instance due to storing the assay at a low temperature for too long, or due to too small amount of DNA in the sample;

Introduction of sequence errors caused by imperfect PCR amplification and cycling, for instance due to temperature changes;

Suboptimal design of the probes or primers. For example, mutations may fall within the regions of the probes or primers;

Enrichment method limitations. For instance, long deletion may span the amplified region;

Cross-contamination of data sets, read loss and decreased read quality due to fragment tagging with barcodes, adapters and various pre-defined sequence tags;

Chimeric reads in long-insert pair-ended reading.

Biases introduced by the sample itself, for instance due to:

Somatic features, in particular in cancer diagnosis based on tumor sample sequencing;

The type of biological sample, e.g. blood, urine, saliva, and associated sample preparation issues, for instance causing degradation of DNA, contamination with alien DNA, or too low DNA input.

Biases introduced by the genomic data structure of certain regions specifically, for instance due to:

High ratio of GC content in the region of interest;

Presence of homopolymers and/or heteropolymers, that is partial genomic sequence repetitions of one or more nucleotides in certain regions, causing ambiguities in initial alignment, and possibly inherent sequencing errors in particular with the Roche 454 and Ion Torrent sequencer technologies;

Presence of homologous and low-complexity regions;

Presence of non-functional pseudogenes that may be confused with functional genes, in particular in high-repeat genomic regions of the human genome when the DNA fragments are not long enough compared to the read length.

This limits the efficient deployment of NGS in routine genomic analysis applications, as a different genomic data analysis workflow need to be manually organized and configured with different sets of parameters by highly specialized personnel for each application to meet the clinical expectations in terms of specificity and sensitivity. The automation of genomic data processing workflows is particularly challenging as the workflows need to take into account the specific data biases introduced by the upstream NGS biological processes on the one hand and the genomic data structures inherent to the current application on the other hand. In early deployment of genomic testing, a limited number of tests and setups were processed by dedicated platforms, which could be manually setup, configured and maintained by highly skilled specialized staff. This approach is costly and does not scale well as more and more tests have to be conducted in daily operation by a single multi-purpose genomic analysis platform.

In terms of automating the NGS analysis, special attention needs to be devoted to the inherent difficulties in characterizing the indel variants in homopolymer and/or heteropolymer regions of the reference human genome, in particular when the laboratory employs pyrosequencing (as in Roche 454 platforms) or semiconductor sequencing (as in Ion Torrent platforms). Mischaracterization of some homopolymer or heteropolymer variants may result in false positive detection of certain traits and diseases in a diversity of diagnosis applications, for instance based on some genetic variations in cancer-related genes, as highlighted for instance by Singh et al. in *"Clinical validation of a Next-Generation Sequencing Screen for Mutational Hotspots in 46 Cancer-Related Genes"*, The Journal of Molecular Diagnostics, Vol. 15, No. 5, September 2013. To overcome this limitation, Singh et al. proposed to exclude variants that have a population frequency of more than 20% of the samples sequenced as most probably biased by the sequencing process. In current NGS practice, the applicants genomic analyzer platform Sophia DDM® may be configured to ignore INDELs located in homopolymer regions greater than 10 bp, as described for instance in the proposal for the evaluation of genetic test for primary lymphoedema with a panel of 15 genes by the London South West RGC St George's Approval date January 2018) or *"Performance characteristics—BRCA MASTR Dx with drMID Dx for Illumina NGS Systems"*, rev. July 2017.

Other bioinformatics solutions such as the Sequence Pilot SeqNext module from JSI Medical Systems GmbH, Kippenheim, Germany may be configured to call variants in homopolymers of at least 6 bp only if the variant frequency exceeds 20% of the reads, as described by Nunziato et al. in *"Fast Detection of a BRCA2 Large Genomic Duplication by Next Generation Sequencing as a Single Procedure: A Case Report"*, Intl J Mol Sci v. 18(11), November 2017. The current practice in NGS gene panel testing thus consists in ignoring or carefully parametrizing variant detection in homopolymer or heteropolymer regions of the human genome when the NGS platform is known to bias them. However, these approaches may result in false negative characterizations. In *"Improved efficiency and reliability of NGS amplicon sequencing data analysis for genetic diagnostic procedures using AGSA software"*, Biomed research international, Vol. 2016, Art ID 5623089, Poulet et al. identifies the limitations of different software analysis workflows such as CORAL, HECTOR, AmpliconNoise for the detection of BRCA gene variants associated with familial breast and ovarian cancer risk and proposes an improvement method (implemented by the authors as the AGSA software) based on parsing the SFF file, collecting the flowgram value for each read for a sample of interest, and deriving a histogram image which can be further inspected by the end user. For a heterozygous insertion or deletion, the distribution of read values is split into two populations, showing that some reads (from one allele) have n identical bases while others (from the other allele) have n+1 (insertion) or n−1 (deletion) identical bases. On the contrary, in case of sequencing bias artefacts, a single population is observed between n and n+1 (or n−1) peaks in the histogram. In the case of homozygous variation, a single population is centered on n+1 (or n−1), showing that all reads have the same number of bases in the homopolymer and that this number is different from the wild type.

Poulet et al. also suggests that the mono- or bimodal distribution of the histogram values may also be evaluated statistically, but do not disclose methods to achieve this. Moreover, their approach requires the analysis of the flow files directly out of the sequencer, which complicates the design and deployment of an automated genomic analyzer workflow platform in a networked computing environment, in particular when the genomic analysis solution is deployed independently from the laboratory equipment, as is for instance the Sophia DDM (Data Driven Medicine) SAAS (Software As A Service) platform.

Similar to the proposal of Poulet et al., a statistical method to better detect insertion and deletion in a homopolymer region and detecting the corresponding heterozygosity was also described in US patent application 2014/0052381 by Utirametur et al. They observed that in an NGS genomic analyzer workflow, the read alignment is not necessarily correct, but it may be possible to determine the heterozygosity from the distribution of base calling residuals based on measured and model-predicted values in the homopolymer regions by using a Bayesian peak detection approach and best-fit model, as homozygous regions tend to have a unimodal distribution while heterozygous regions tend to have a unimodal distribution. From the best-fit model, it is also possible to derive the homopolymer length value for both alleles in the homozygous (unimodal distribution) case, or two different homopolymer length values, one for each allele, in the heterozygous case (bimodal distribution). While this method may facilitate the identification of the length of short homopolymer regions as the associated flow space densities clearly exhibit a peak value, we observed that it is significantly more difficult to classify longer homopolymers as well as heteropolymers.

There is therefore a need for a better solution to automatize the genomic data processing variant calling workflows for data-driven medical applications, so that the same genomic data processing platform may operate on a diversity of genomic data as may be generated from different next-generation sequencing laboratory setups while optimizing the specificity and the sensitivity of the variant calling results to improve research and clinical practice over the prior art methods in genomic data contexts involving the challenging characterization of homopolymer and/or heteropolymer repeat patterns variants.

BRIEF SUMMARY

A method is proposed for detecting and reporting, with a processor, a variant as the repeat of at least two nucleotide patterns in the genomic sequence of a patient sample, the method comprising:

(a) identifying a reference repeat pattern $P_{ref}=N*l$ as the repeat of l (l>=2) genomic patterns N in a genomic region of a human genome reference sequence;

(b) obtaining, with a next generation sequencer, n patient sets of next generation sequencing data reads covering the reference repeat pattern genomic region S={S_1, S_2, . . . , S_i, . . . , S_n} from a pool of n enriched genomic patient samples, each set S_i being associated with a patient sample, the number n of enriched genomic patient samples being at least 4;

(c) for each patient sample i in the set S of patient samples, measuring the distribution P_i of the length of the repeat pattern in the set of next generation sequencing reads S_i;

(d) for a possible pair of patient samples i and j, j>i, estimating a best-fit model $$[V_{ij}^1|V_{ij}^2]$$

of the two allele variants for sample i relative to sample j, with a confidence level L_{ij};

(e) for each possible triplet of patient samples i, j>i, k>j, comparing their respective best-fit models $$[V_{ij}^1|V_{ij}^2], [V_{jk}^1|V_{jk}^2], [V_{ik}^1|V_{ik}^2],$$

grouping matching best-fit models into groups of best-fit variant models with an increased confidence level, and iterating the comparison until stable groups of best-fit variant models are formed;

(f) identifying the most likely group carrying the wild type variant;

(g) for each sample in the group carrying the wild type variant, reporting the sample variant as the wild type reference repeat pattern $P_{ref}=N*l$.

(h) for each sample out of the group carrying the wild type variant, unbiasing the best-fit variant model of the group comprising this sample as a function of the best-fit variant model for the identified wild type group, and reporting the sample variant as the unbiased variant.

BRIEF DESCRIPTION OF THE DRAWINGS

FIG. 4 illustrates the probability distribution of the measured relative length of a repeat pattern variant relative to the human genome reference (centered on 0) as may be measured subject to experimental error, respectively for samples having no mutation (top table) and for samples with a heterozygous deletion on allele 1 (bottom table).

FIG. 10 shows an exemplary table of matching 8 samples respectively to each other assumed as the reference, where samples S1, S2 and S3 match each other as not carrying any mutation (0/0).

FIG. 11 shows another exemplary table of matching 8 samples respectively to each other assumed as the reference, where samples S2, S7 and S8 only partly march each other, S2 vs S7 and S7 vs S8 without any mutation (0/0), yet S2 vs S8 carrying a heterozygous mutation (−1/0).

FIG. 12 shows another exemplary table of matching 8 samples respectively to each other assumed as the reference, where samples S1, S2 and S6 do not match each other and no relevant match can be found between S2 and S6 (NA/NA).

FIG. 13 shows another exemplary table of matching 8 samples respectively to each other assumed as the reference, after iterating the proposed matching method.

FIG. 14 illustrates a possible grouping of samples in an exemplary table of matching 8 samples respectively to each other assumed as the reference.

DETAILED DESCRIPTION

Next Generation Sequencing Analysis System

Figure 1:
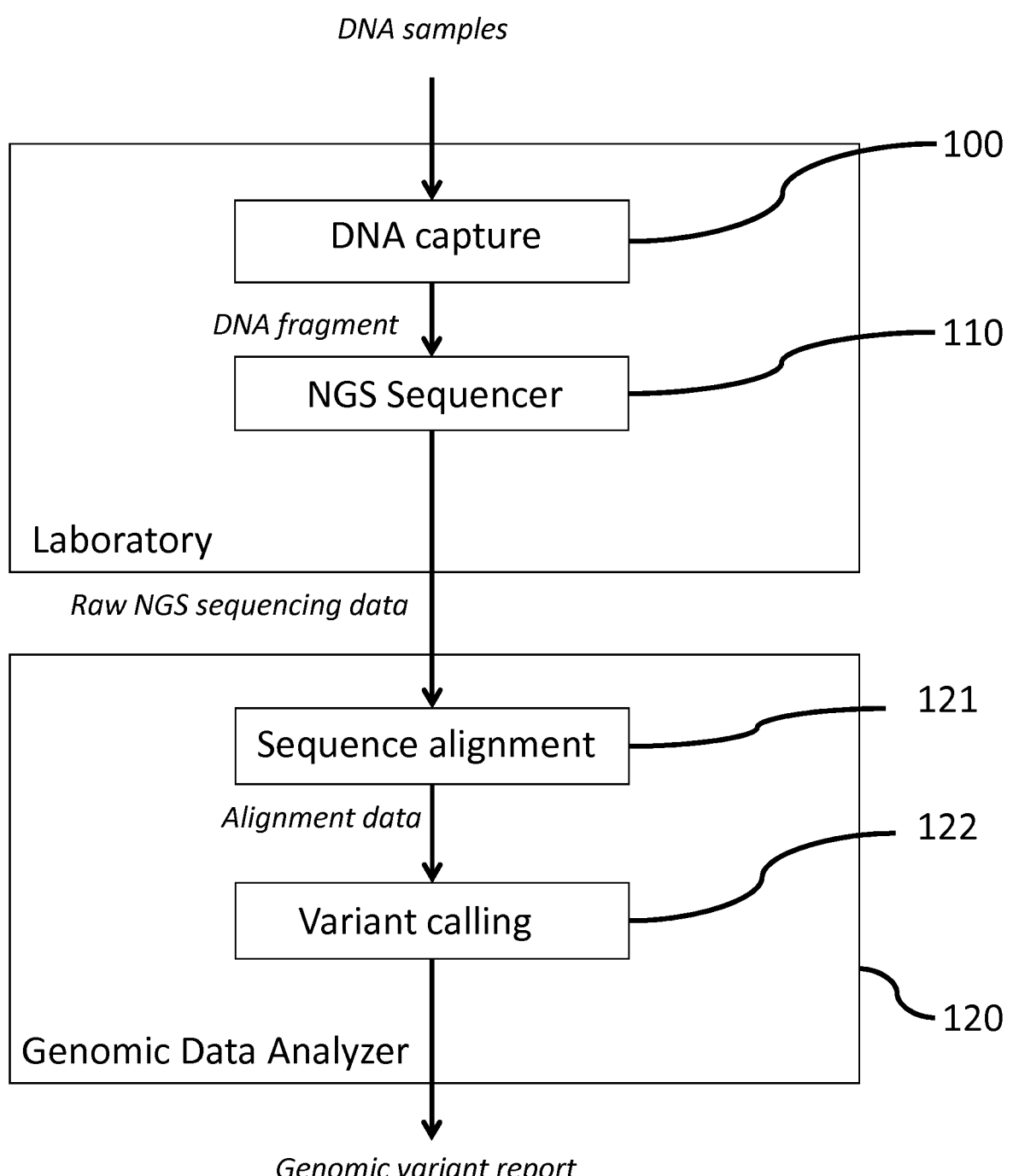
FIG. 1 represents a prior art next generation sequencing system.

FIG. 1 shows an exemplary genomic analysis system comprising a DNA enrichment assay 100, a next generation sequencer 110 and a genomic data analyzer 120.

In an NGS laboratory, a pool of DNA samples is processed by the DNA enrichment assay 100 to generate a library of pooled amplicons (for amplicon-based enrichment) or fragments (for probe-based enrichment) as DNA fragments input to the next generation sequencer 110, each set of amplicons/fragments corresponding to a different sample. The number of amplicons/fragments is application dependent. In some genomic analysis experiments, target enrichment may require 150 primers to enrich 75 different regions to be targeted out of the sample genome, resulting in a set of 75 amplicons for each sample. The number of samples may also be adapted to the next-generation sequencing sequencer 110 parallel processing capability, for instance 48 samples in the form of a library of pooled amplicons may be sequenced in parallel by an Illumina MiSeq sequencer. Other NGS sequencer technologies may be used, such as for instance the Roche 454™ GS Junior or GS FLX, Illumina MiSeq®, or Life Technologies Ion PGM™ sequencers.

The next-generation sequencer 110 analyses the input samples and generates sequence reads in a computer-readable file format representing raw NGS sequencing data. Depending on the NGS technology, one or more files may be output by the NGS sequencer 110. In some embodiments, for instance with Illumina sequencers, the FASTQ file format may be used with two different files for forward and reverse reads or as a single joined file. This text file typically starts with a sequence header marked by a '@' start character, followed by one line of sequence information represented as a string of 'A', 'T', 'C', 'G' nucleotide characters, then by a quality header marked by a '+' start character, followed by one line of quality metrics, one quality score matching each nucleotide read. The format for the quality metrics for each nucleotide in the sequence information string may depend on the sequencer. Some legacy sequencers output the raw sequencing data in the SFF (Standard Flowgram Format) binary file format, which comprises an informative header and the read data. Other embodiments are also possible, for instance some legacy Roche sequencers output multiple FASTQ files for a single patient analysis, while other sequencers, for instance the Ion Torrent PGM sequencers, have migrated to the compressed unmapped BAM file format, as may be recognized from the .basecaller.bam file extension. As known to those skilled in the art of communication systems, the laboratory operates a computing infrastructure to store the resulting raw NGS sequencing data file in a laboratory biobank. The laboratory computing infrastructure connects, with authentication credentials, through a communication network, to the genomic data analyzer 120 and transmits a genomic analysis request comprising the raw NGS sequencing file to the genomic data analyzer 120.

The genomic data analyzer 120 computer system (also "system" herein) 120 is programmed or otherwise configured to implement different genomic data analysis methods, such as receiving and/or combining sequencing data and/or annotating sequencing data.

The genomic data analyzer 120 may be a computer system or part of a computer system including a central processing unit (CPU, "processor" or "computer processor" herein), memory such as RAM and storage units such as a hard disk, and communication interfaces to communicate with other computer systems through a communication network, for instance the internet or a local network. Examples of genomic data analyzer computing systems, environments, and/or configurations include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and the like. In some embodiments, the computer system may comprise one or more computer servers, which are operational with numerous other general purpose or special purpose computing systems and may enable distributed computing, such as cloud computing, for instance in a genomic data farm. In some embodiments, the genomic data analyzer 120 may be integrated into a massively parallel system. In some embodiments, the genomic data analyzer 120 may be directly integrated into a next generation sequencing system.

The genomic data analyzer 120 computer system may be adapted in the general context of computer system-executable instructions, such as program modules, being executed by a computer system. Generally, program modules may include routines, programs, objects, components, logic, data structures, and so on that perform particular tasks or implement particular abstract data types. As is well known to those skilled in the art of computer programming, program modules may use native operating system and/or file system functions, standalone applications; browser or application plugins, applets, etc.; commercial or open source libraries and/or library tools as may be programmed in Python, Biopython, C/C++, or other programming languages; custom scripts, such as Perl or Bioperl scripts.

Instructions may be executed in distributed cloud computing environments where tasks are performed by remote processing devices that are linked through a communications network. In a distributed cloud-computing environment, program modules may be located in both local and remote computer system storage media including memory storage devices.

As illustrated on FIG. 1, the genomic data analyzer 120 may comprise a sequence alignment module 121, which compares the raw NGS sequencing data to a reference genome. The sequence alignment module 121 may be configured to execute different alignment algorithms. Standard raw data alignment algorithms such as Bowtie2 or BWA that have been optimized for fast processing of numerous genomic data sequencing reads may be used, but other embodiments are also possible. The alignment results may be represented as one or several files in BAM or SAM format, as known to those skilled in the bioinformatics art, but other formats may also be used, for instance compressed formats or formats optimized for order-preserving encryption, depending on the genomic data analyzer 120 requirements for storage optimization and/or genomic data privacy enforcement.

The resulting alignment data may be further filtered and analyzed by a variant calling module 122 to retrieve variant information such as SNP and INDEL polymorphisms. The variant calling module 122 may be configured to execute different variant calling algorithms. The resulting detected variant information may then be output by the genomic data analyzer module 120 as a genomic variant report for further processing by the end user, for instance with a visualization tool, and/or by a further variant annotation processing module (not represented).

The genomic data analyzer 120 may be adapted to automatically detect, with a processor, a set of characteristics that uniquely determine the input sequencing data and corresponding genetic context, the DNA enrichment context such as the sample type or laboratory process characteristics, the DNA enrichment technology such as the targeted enrichment target kit or capture probe assay characteristics, and/or the NGS sequencing technology. As will be apparent to those skilled in the art of next generation sequencing, these experimental characteristics may cause specific biases in the sequence alignment and/or the variant calling results.

The proposed genomic data analyzer system 120 may thus serve next generation sequencing genomic analysis requests from different labs that are independently operating different sequencer technologies and different DNA enrichment technologies on different samples for different genes. The proposed genomic data analyzer system 120 may automatically detect a set of characteristics from the input data and requests received from the laboratory and may adapt the configuration of the sequence alignment module 121 and the variant calling module 122 accordingly, without requiring a time consuming and costly manual setup to minimize the data biases possibly induced by each different biological workflow. As will be apparent to those skilled in the art, there may be dozens or even hundreds of different clinical laboratory setups for multiple sourcing laboratories operating with the same genomic analyzer 120, and this number and diversity is likely to further increase with the deployment of additional technologies and assays as the NGS-based personalized medicine clinical practice develops.

Depending on the detected genomic experiment characteristics, the genomic data analyzer 120 may configure the sequence alignment module 121 to operate additional data processing steps and/or use different sets of configuration parameters such that the data biases caused by the genomic experiment characteristics are minimized.

Depending on the detected input characteristics, the genomic data analyzer may further configure the variant calling module 122 to operate additional data processing steps and/or use different sets of configuration parameters such that the data biases caused by the genomic experiment characteristics are minimized.

Depending on the results of the initial sequence alignment by the sequence alignment module 121, the genomic data analyzer 120 may be further adapted to identify next generation sequencing data alignment biases that become apparent when analyzing the alignment data. The genomic data analyzer may accordingly configure the sequence alignment module 121 to execute an additional step of re-alignment of the raw NGS sequencing data. This re-alignment may be constrained by additional parameters as may be determined from the initial alignment results. In a possible embodiment the re-alignment is applied specifically on a sub-region of the genomic sequence. The resulting re-alignment data may be further filtered and analyzed by the variant calling module 122 to output a more relevant genomic variant report with increased sensitivity and specificity for variant detection.

Depending on the results of the variant calling by the variant calling module 122, the genomic data analyzer 120 may be further adapted to identify variant calling biases that become apparent when calling variants on the alignment data. The genomic data analyzer may accordingly configure the variant calling module 122 to execute an additional step of re-calling variants on all or part of the alignment data. This refined variant calling step may be constrained by additional parameters as may be determined from the former alignment and/or re-alignment and/or variant calling results. In a possible embodiment, variants are specifically called on a subset of the aligned genomic data. The resulting refined variant calling data may be further combined with the standard variant calling results by the variant calling module 122 to output a more relevant genomic variant report with increased sensitivity and specificity for variant detection. In a possible embodiment, some variant calling results may be excluded from the genomic variant report as identified possibly biased by the variant calling module 122, so that a more relevant genomic variant report is generated by the genomic data analyzer 120 with increased sensitivity and specificity for variant detection.

Figure 2:
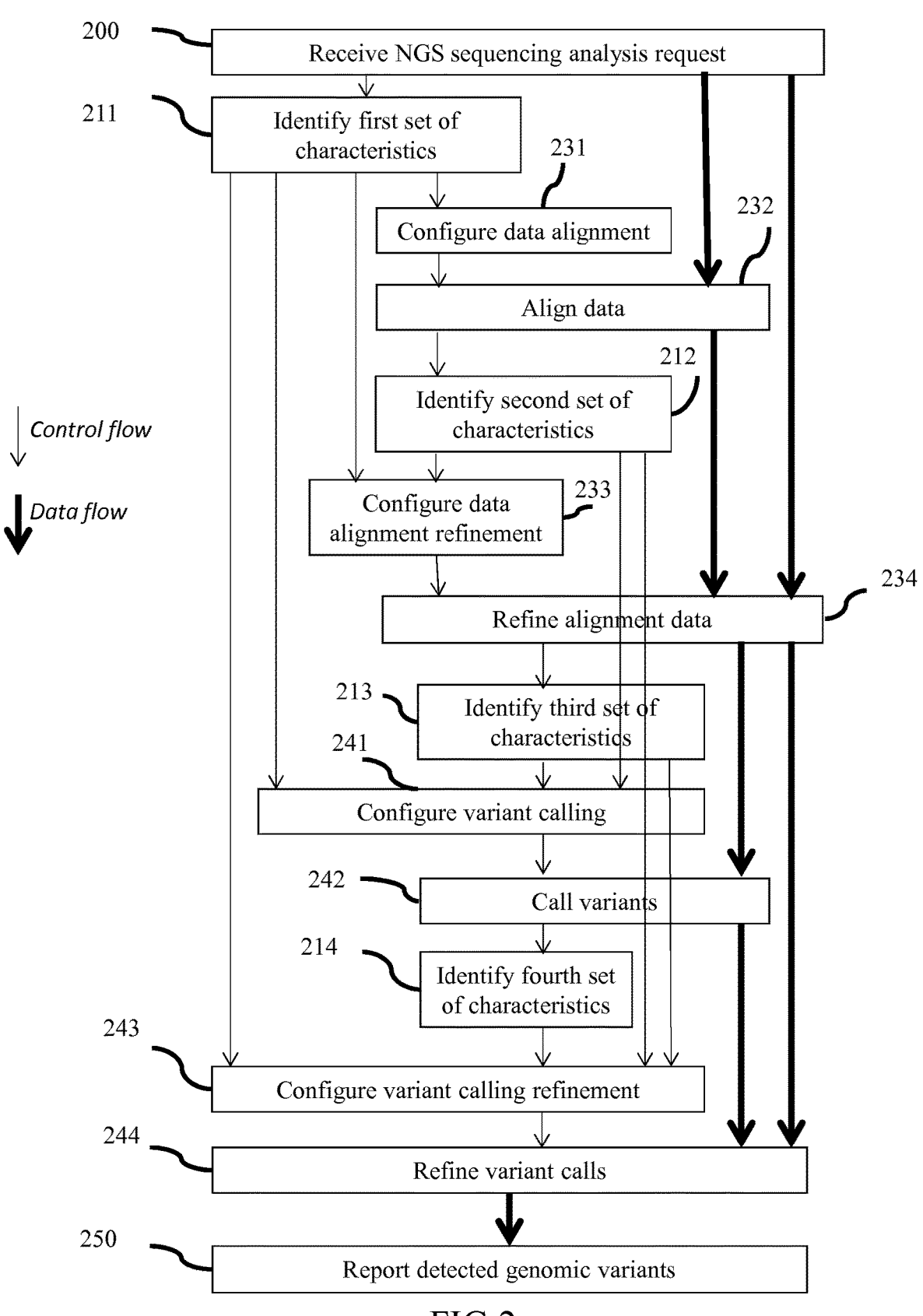
FIG. 2 shows the flowchart of a next generation sequencing genomic analysis workflow.

FIG. 2 shows accordingly a possible genomic analysis workflow for the genomic data analyzer 120, comprising:

receiving 200 a next generation sequencing analysis request;

identifying 211 a first set of characteristics associated with the next generation sequencing analysis request, the first set of characteristics comprising at least a target enrichment technology identifier, a sequencing technology identifier, and a genomic context identifier;

configuring 231 a data alignment module 121 to align the input sequencing data in accordance with at least one characteristic of the first set of characteristics;

aligning 232, with the configured data alignment module 121, the input sequencing data to a genomic sequence, and reporting the alignment data into a raw alignment data file;

identifying 212 a second set of characteristics associated with the alignment data from the raw alignment data file, the second set of characteristics comprising at least a data alignment pattern identifier;

configuring 233 the data alignment module 121 to refine at least one subset of the input sequencing data in accordance with at least one characteristic of the first set of characteristics and at least one characteristic of the second set of characteristics;

refining 234, with the configured data alignment module 121, the subset of the input sequencing data to produce a refined alignment data file;

identifying 213 a third set of characteristics associated with the re-alignment data from the refined alignment data file, the third set of characteristics comprising at least a genomic context identifier;

configuring 241 a variant calling module 122 to detect variants associated with the refined alignment data in accordance with at least one characteristic of the first set of characteristics, at least one characteristic of the second set of characteristics, and at least one characteristic of the third set of characteristics;

detecting 242 a first set of genomic variants, with the configured variant calling module 122, in the refined alignment data;

identifying 214 a fourth set of characteristics associated with the detected genomic variants, the fourth set of characteristics comprising at least a variant calling refinement identifier;

configuring 243 the variant calling module 122 to detect variants associated with the refined alignment data in accordance with at least one characteristic of the first set of characteristics, at least one characteristic of the second set of characteristics, at least one characteristic of the third set of characteristics and at least one characteristic of the fourth set of characteristics;

detecting 244 refined genomic variants, with the configured variant calling module 122, in the refined alignment data and the detected genomic variants, to produce a refined set of genomic variants;

reporting 250 the refined set of genomic variants.

The generic, multi-purpose genomic data analyzer 120 thus facilitates the analysis and reporting of multiple different genomic variants from raw next generation sequencing data received from a diversity of clinical setups operated by multiple sourcing laboratories without requiring dedicated manual configuration or exhaustive metadata documentation to adapt to each combination of biological setup and diagnosis context for each clinical analysis.

Refined Variant Calling Method—Exemplary Workflow

An exemplary embodiment of the proposed refined variant calling method 244 for more accurate repeat patterns (homopolymers and/or heteropolymers) variant identification will now be described in more detail. The fully automated genomic data analysis workflow of FIG. 2 operates on genomic data sourced from at least one next generation sequencing laboratory.

As an example, the laboratory may operate an Ion Torrent sequencer and the Integrated DNA Technologies' xGen Lockdown Probes to identify genomic variants in up to 27 genes possibly relevant to breast, ovarian, and gastrointestinal hereditary cancers. As will be apparent to those skilled in the art of human genomics, some of those genomic variants correspond to fairly long homopolymer regions in the wild type human reference chromosomes, such as for example (non-exhaustive list) the repeat of 13 A nucleotides on the CHEK2 genomic region at position 29130814 of chromosome 22; the repeat of 14 T nucleotides on the RAD54L genomic region at position 46739975 on chromosome 1; or the repeat of 19 T nucleotides on the ATM genomic region at position 108195977 on chromosome 11.

As another example, the laboratory may operate an Illumina MiSeq® sequencer with "the Multiplicom CFTR MASTR™ Dx assay as the target enrichment technology to identify genomic variants in the CFTR gene covered by this specific amplicon-based kit. The number of repeats in TG dinucleotides (heteropolymers) is typically 11 in the CFTR gene of human chromosome 7, but may vary from 9 (2 deletions) to 14 (3 insertions) repeats. The latter variants influence the splicing of exon 9 in the CFTR gene and have been associated with the cystic fibrosis disease when the CFTR gene also carries an abbreviated variant of only 5T homopolymers on the polythymidine tract, which is typically of 7 T nucleotide repeats, but may vary from 5 to 9 T nucleotide repeats. Moreover, 12 or 13 TG heteropolymer repeats are also associated with some less common cystic fibrosis pathology, while 11 TG dinucleotides repeats are less associated with the disease (Hefferon et al, "*A variable dinucleotide repeat in the CFTR gene contributes to phenotype diversity by forming RNA secondary structures that alter splicing*", Proc Natl Acad Sci USA 101:3504-3509, 2004.

As a function of at least one of the first characteristics, namely the target enrichment technology identifier, the sequencing technology identifier, and/or the genomic context identifier, the genomic data analyzer 120 configures 231 the data alignment module 121 to execute 232 a first raw data alignment. The data alignment module 121 may also execute 232 pre-processing steps such as removing the assay specific adapters from the reads. The data alignment module 121 aligns 232 to a reference genomic sequence, with a raw data alignment algorithm as known to those skilled in the art of bioinformatics, the pre-processed raw sequencing data to produce a data alignment file. Standard algorithms such as Bowtie2 or BWA that have been optimized for fast processing of numerous genomic data sequencing reads may be used, but other embodiments are also possible. The resulting data alignment file may be represented as one or several files in BAM or SAM format, but other embodiments are also possible, in particular the data alignment module 121 may also execute 232 post-processing steps such as compressing and/or encrypting the alignment data, for instance with an order-preserving encryption, a homomorphic encryption, a symmetric encryption and/or an asymmetric encryption scheme and/or a combination thereof, depending on the genomic data analyzer 120 requirements for storage optimization and/or genomic data privacy enforcement along the genomic analysis workflow processing.

The genomic data analyzer 120 may then automatically derive 212 a second set of characteristics from the results of data alignment 232, such as a specific data alignment pattern requiring refinement of the alignment and/or the variant calling algorithms. The genomic data analyzer may for instance detect the presence of alignment mismatches especially at the beginning and/or the end of the reads ("soft clipping"), as may be due to primer mispriming. This frequent bias in amplicon-based technologies may indeed cause either:

False positives, when a mispriming artifact is present in enough reads to be misaligned to the reference genome, which will cause a wrong variant calling 242 interpretation as a SNP in the DNA sample;

False negatives, when the alignment module 121 cannot discriminate between mispriming artifacts in certain reads and the correct amplicon data in other reads, causing the corresponding regions to be soft clipped by the data alignment module 121, which will in turn cause the variant calling 242 to miss possible variants of pathological relevance in the correct amplicon data.

Soft clip patterns correspond to sequencing data at the 5' or 3' boundaries of the reads that could not be properly aligned by the data alignment module 121 raw alignment algorithms 232. Soft clipped alignments are specifically marked in the CIGAR string of the alignment data file, so the corresponding patterns can be easily identified after data alignment 232. As known to those skilled in the art of Next Generation Sequencing, soft clipping information may then be re-mapped in the genomic analysis workflow with specific algorithms in order to further detect structural variants of potential clinical relevance.

The genomic data analyzer 120 may thus automatically identify 212 the reads with soft clipping regions, from the results of the data alignment 232, and configure 233 the data alignment module 121 to operate a further data re-alignment 234 on those reads specifically by taking into account the primer anchors information corresponding to the specific DNA enrichment technology, in the alignment algorithm. As will be apparent to those skilled in the art of bioinformatics, a more robust algorithm than Bowtie2 or BWA may be used specifically on those regions, even if less computationally efficient. Indeed, only a subset of the whole NGS data needs to be re-aligned this way and the proposed workflow is fully automatized, so the overall computational efficiency performance of the genomic data analyzer 120 is not be significantly impacted, while this data re-alignment refinement automation enables to increase the specificity and sensitivity of the genomic data analyzer 120 to be comparable to that obtained with manual trial-and-errors setups of the prior art research practice. Examples of such algorithms have been described for instance by Suzuki et al. in "*ClipCrop: a tool for detecting structural variations with single-base resolution using soft-clipping information*", *BMC Bioinformatics* 2011 12(*Suppl* 14):*S7* and by Schröder et al in "*Socrates: identification of genomic rearrangements in tumour genomes by re-aligning soft clipped reads*", *Bioinformatics* (2014), but other embodiments are also possible. In particular the most efficient re-alignment algorithm may be automatically configured 233 by the proposed genomic data analyzer 120 as a function of both the genomic context and the raw alignment data soft clip patterns.

Depending on the genomic context identifier, the genomic data analyzer 120 may also identify from the alignment data the presence of some regions that are particularly challenging to align, such as homopolymer regions, heteropolymer regions, or more generally any regions with specific repeat patterns. Proper alignment of corresponding next generation sequencing reads is particularly challenging as those multiple repeats cause alignment ambiguities. The genomic data analyzer 120 may thus automatically identify 212 from the results of the raw data alignment 232 a specific genomic context requiring refinement on the reads overlapping those ambiguous regions. The genomic data analyzer 120 may accordingly configure 233 the data alignment module 121 to operate a further data re-alignment 234 on those reads to identify other possible alignment solutions, such as for instance by taking into account the PCR error rate and comparing reads to each other.

The genomic data analyzer 120 may then use the target enrichment technology identifier to configure 241 the variant calling module 122 to execute different variant calling algorithms in accordance with the initially identified genomic context identifier (e.g. CHEK2, ATM, BRCA2, CFTR . . . ) and the specific genomic context refinement identified from the raw alignment results (e.g. the presence of certain homopolymer repeat patterns in the data). The variant calling module 122 calls 242 variants on the refined alignment data to produce a first VCF file. In some cases, the resulting variants may not be accurate enough to be reported by the genomic data analyzer 120.

A possible embodiment of a refined variant calling method 244 suitable to better identify repeat pattern tracts will now be described in more detail. As known to those skilled in the art of bioinformatics, the genomic data analyzer 120 may receive from the laboratory raw NGS sequencing data corresponding to a diversity of patients whose samples have been pooled in the same sequencing run. Due to the lower DNA sequencing experiment accuracy in the presence of homopolymer or heteropolymer nucleotide repeats, false insertions and deletions may be detected even when there was actually no mutation in the samples. In state of the art laboratory practice, up to 30% of the homopolymers may be missing thus analyzed as deletions due to sequencing errors in those regions, which introduces a significant statistical bias and thus decreases the accuracy of the genomic analysis. Some laboratories may also sequence control data of a wild type sample in addition to the patient data, all being generated with the same experimental process (DNA capture 100 and NG sequencer 110), so that the control data reference may be used to unbias the data and facilitate the variant calling even in repetitive genomic contexts which are particularly challenging to characterize, as described for instance in the co-pending European patent application WO/2018/104466. However, depending on the laboratory setup, control data may not be available. In such a setup, accurate variant calling is challenged by the difficulty in properly estimating the length of the repetitive sequence patterns, such as for example the A homopolymer tract on the CHEK2 gene, the T homopolymer tract on the RAD54L gene, the T homopolymer tract on the ATM gene, or the TG heteropolymer tract on the CFTR gene without any hint on the underlying sequencing errors potentially biasing the measurements. Indeed, the measured length of the repeat pattern follows a discrete probability distribution of the length of the repeat patterns ("distribution-length") that may depend both on the experiment bias and the actual genomic variant. For increased sensitivity and specificity in the genomic analysis workflow, it is desirable to decrease the contribution of the experiment bias in the measurement data as much as possible. This may be achieved by cross-analyzing sample measurements under the assumption than one of them corresponds to the human genome reference (i.e., not carrying any variant). The assumed reference sample measurement may then be used as the reference data to predict variant models, to which the refined variant calling method 244 may then match the measurements of each other sample, thus enabling a more accurate variant identification for those samples.

As described for instance in the co-pending European patent application EP 16202691.8, the distribution of the length may be measured as the discrete probability distribution of the absolute length of a repeated pattern in a set of genomic sequence data reads with sufficient coverage. In another possible embodiment the distribution length may be measured as the discrete normalized probability distribution of the relative length (indicating deletions or insertions) of a repeated pattern in a set of genomic sequence data reads with sufficient coverage, relative to the theoretical human genome reference pattern, (also corresponding to wild type samples most commonly found without mutation). Throughout this disclosure, relative length will be considered to facilitate the understanding of the proposed methods, however as will be apparent to those skilled in the art, the proposed methods also apply to absolute length measurements as a simple shift of relative length measurements.

Depending on the genomic context, the repeat pattern may be a homopolymer, as the repetition of a single nucleotide. In the CHEK2 genomic analysis application, the homopolymer may be the poly-A pattern, the absolute length for this pattern may usually be measured in the range of 11 to 15 repeats, or the relative length in the range of −2 (2 deletions) to +2 (2 insertions) with 0 representing the wild type repeat pattern of 13 A nucleotides without mutation. In the RAD54L genomic analysis application, the homopolymer may be the poly-T pattern, the absolute length for this pattern may usually be measured in the range of 9 to 13, or the relative length in the range of −2 (2 deletions) to +2 (2 insertions) with 0 representing the wild type repeat pattern of 11 T nucleotides without mutation. In the ATM genomic analysis application, the homopolymer may be the poly-T pattern, the absolute length for this pattern may usually be measured in the range of 17 to 21, or the relative length in the range of −2 (2 deletions) to +2 (2 insertions) with 0 representing the wild type repeat pattern of 19 T nucleotides without mutation.

Depending on the genomic context, the repeat pattern may also be a heteropolymer, as the repetition of a pair or triplet or more nucleotides. In the CFTR example, the repeat pattern may be the TG heteropolymer repeat, the absolute length range for this pattern may be 11 In the CFTR genomic analysis application, the heteropolymer may be the dinucleotide TG pattern, the absolute length for this pattern may usually be measured in the range of 9 to 14, or the relative length in the range of −2 (2 deletions) to +3 (3 insertions) with 0 representing the wild type repeat pattern of 11 TG dinucleotides without mutation.

In the exemplary applications of CHEK2, RAD54L or ATM, and CFTR genomic analysis respectively, the refined variant calling method 244 may evaluate the length for the poly-A homopolymer tract, the poly-T homopolymer tract, or the poly-TG heteropolymer tract respectively, to better characterize the corresponding genomic variant. In order to accurately estimate the length of the pattern repeats, the variant calling method 244 should minimize the biases caused by the experiment errors. This may be achieved by estimating the expected distribution-lengths for various insertion and deletion scenarios on each possible repetitive sequence pattern for different hypotheses on the input data and selecting the best match ("best-fit variant model").

As will be apparent to those skilled in the art of bioinformatics, this method will significantly improve the accuracy of the repetitive pattern length estimation provided that the next generation sequencing reads have a large enough statistical coverage. It will also be apparent to those skilled in the art of biology that there is no simple method for a human operator to identify the wild type reference and/or the actual length of the repeat pattern tracts in the patient DNA samples, thus there is a significant advantage in employing a signal processing automation method, with one or more computer processors, to facilitate the actual analysis of the patient DNA sample data as sequenced with a Next Generation Sequencer.

Under the assumption that the biases equally apply to all samples in the pool of samples, it will in particular also apply to the wild type samples. We therefore propose to best-fit variant models on sample data relative to another sample in the pool, assumed to correspond to the wild type sample. In the method of the co-pending European patent application EP 16202691.8, the wild type sample is the control data sample. If no control data sample is present in the pool, different hypotheses may be conducted and verified by cross-analyzing each sample relative to the other samples, as will now be disclosed in further detail.

Sample-to-Sample Best Fitting of Variant Models

Figure 3:
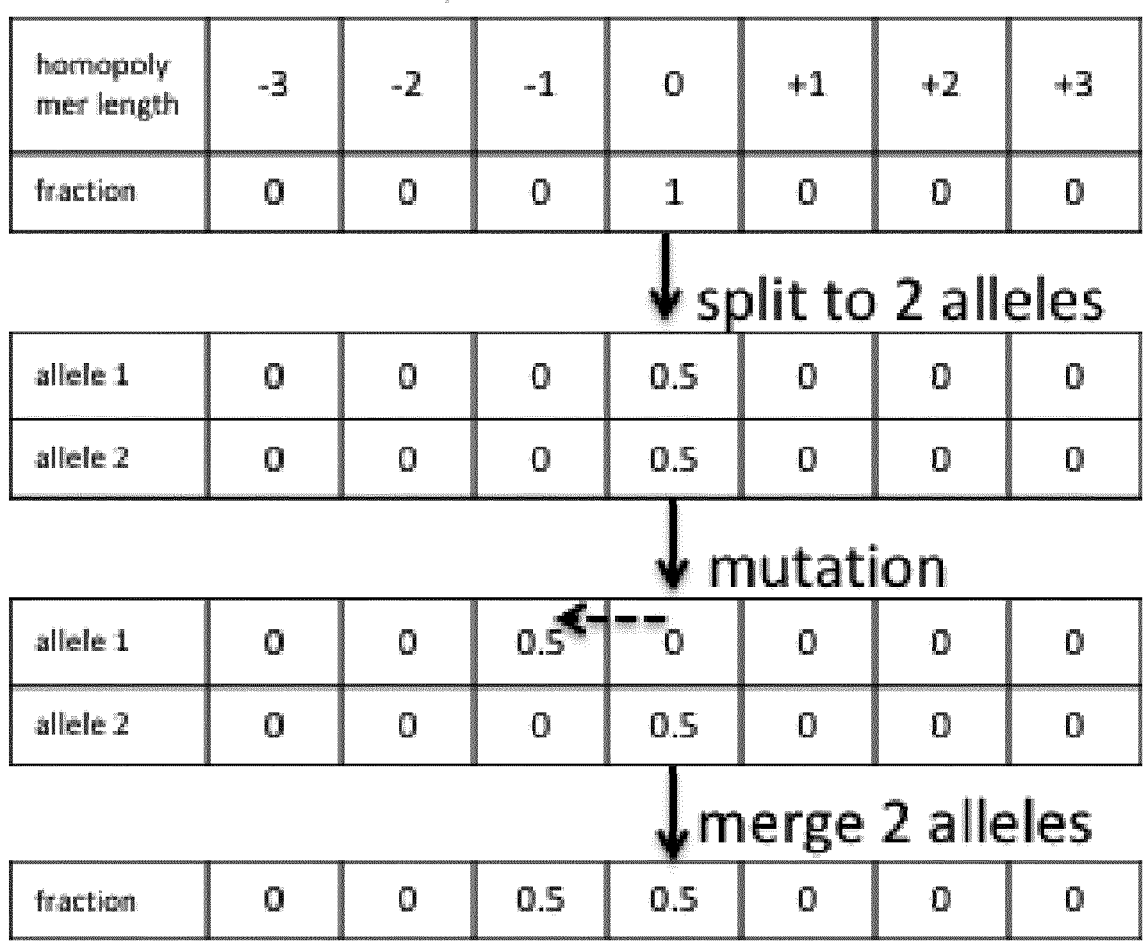
FIG. 3 illustrates the probability distribution of the expected relative length of a repeat pattern variant relative to the human genome reference (centered on 0) with no experiment error, respectively for samples having no mutation (top table) and for samples with a heterozygous deletion on allele 1 (bottom table).

A theoretical distribution of the length of a repeat pattern tract in patient samples relative to a repeat pattern tract in the human genome reference is illustrated by FIG. 3 respectively for a control data sample with no mutation and no experiment error bias, and a scenario of a single basic motif deletion mutation, for instance the deletion of one nucleotide in a single allele in the homopolymer genomic region CHEK2 (reference homopolymer pattern length REF=13) or ATM (reference homopolymer pattern length REF=19), or the deletion of one dinucleotide (two nucleotides) in a single allele in the heteropolymer genomic region CFTR (reference heteropolymer pattern length REF=11). This heterozygous deletion is represented as a −1 repeat pattern length difference on one allele relative to the reference, and 0 repeat pattern length difference on the other allele. This corresponds to the ideal, theoretical case where each allele contributes 50% of the distribution-length measurement, thus respectively a length of (REF-1) repeat patterns and a length of REF repeats are expected to be measured from the re-alignment data, each with an equal probability of 0.5 in the normalized discrete probability distribution of the length of the repeat pattern tract.

An exemplary measured distribution of the length of the same repeat pattern tract in patient samples relative to a repeat pattern tract in the human genome reference is illustrated in FIG. 4 respectively for an experimental data set with no mutation but subject to an experiment error bias, which causes (top table of FIG. 4) erroneous shorter lengths measurements of 2 deletions (10% of the control coverage data) or 1 deletion (20% of the control coverage data) and erroneous longer lengths measurements of 1 insertion (10% of the control coverage data), so that only 60% of the coverage data corresponds to the actual length of the repetitive region, for instance an actual length of REF=13 A nucleotides for the standard homozygous 13-A pattern with no mutation on the CHEK2 gene in the human genome reference or an actual length of REF=19 T nucleotides for the standard homozygous 19-T pattern with no mutation on the ATM gene in the human genome reference. The measured discrete probability distribution of the pattern length for the patient data will be biased accordingly, and this experiment-induced bias may thus be taken into account in estimating the expected discrete probability distribution of the pattern length for each possible mutation variant scenario for improved sensitivity and specificity. As an example, the bottom table of FIG. 4 shows the resulting expected discrete probability distribution of the pattern length estimation for the scenario of a single basic motif deletion relative to the human genome reference, for instance the deletion of one nucleotide in a single allele in the CHEK2 gene poly-A homopolymer tract or the ATM or RAD54L gene poly-T homopolymer tract (heterozygous deletion pattern length=REF-1 on one allele, and pattern length=REF on the other allele). On the mutated allele 1 the whole probability distribution of the pattern length may be shifted towards the left, due to the actual deletion of a nucleotide basic motif. As both alleles equally contribute to the overall measurement data, their contributions may be simply summed up and averaged to provide the expected probability distribution of the pattern length for this single deletion mutation scenario, while taking into account the experiment error bias from the wild type data: in this example illustration, we can expect that 5% of a single-deletion mutation patient data will be measured as carrying 3 deletions, 15% as carrying 2 deletions, 40% as carrying 1 deletion (correct result), 35% as carrying no mutation, and 5% as carrying a single insertion of the basic motif, for instance the T nucleotide in the poly-T homopolymer tract on the RAD54L or the ATM genes, or the TG dinucleotide in the poly-TG heteropolymer tract on the CFTR gene.

FIG. 5a) shows exemplary expected discrete probability distributions of the repeat pattern lengths relative to the genome reference repeat pattern length for a diversity of genomic variant scenario models ranging from a homozygous double deletion (top left length of −2 compared to the reference centered on 0) to a homozygous double insertion (bottom right length of +2 compared to the reference centered on 0) when the experiment bias causes the following erroneous probability distribution measurement even in the wild type data with no mutation (0/0 scenario): 40% measurement of no mutation, 30% measurement of a single deletion (length of −1 compared to the reference centered on 0), 30% measurement of a single insertion (length of +1 compared to the reference centered on 0).

As will be apparent to those skilled in the art of statistics, the variant calling module 122 may thus apply different methods, for instance a statistical distance measure, to compare the measured normalized discrete probability distribution of the length in the patient data, as illustrated for instance by FIG. 5b), with the expected normalized discrete probability distribution of the length for each scenario, as illustrated for instance by FIG. 5a). The variant calling module 122 may then select the closest comparison scenario as the variant scenario which results in the minimal estimated distance (best-fit model).

Either the relative lengths (number of insertions or deletions relative to the wild type repeats length l in the human genome reference) or the absolute lengths may be used for representing the distributions, one being a simple shift of the reference coordinates compared to the other. A variant scenario of $R_1$ repeats of a nucleotide pattern in the first allele and $R_2$ repeats in the second allele may thus be noted as a variant scenario $[R_1|R_2]$ in absolute coordinates, or as $[V_1|V_2]=[R_1-l|R_2-l]$ in relative coordinates, where l is the number of repeats in the human genome reference.

Thus, in a possible embodiment, the statistical distance between the measured discrete probability distribution of the length in the patient data and the expected discrete probability distribution of the length for a variant scenario $[R_1|R_2]$ of $R_1$ repeats of a nucleotide pattern in the first allele and $R_2$ repeats in the second allele may be computed as the Euclidean distance between the vectors representing their respective normalized discrete probability distributions. Alternately, in a possible embodiment, the statistical distance between the measured discrete probability distribution of the length in the patient data relative to the human genome reference and the expected discrete probability distribution of the length for a variant scenario $[V_1|V_2]=[R_1-l|R_2-l]$ of $R_1$ repeats of a nucleotide pattern in the first allele and $R_2$ repeats in the second allele may be computed as the Euclidean distance between the vectors representing the respective probability distributions.

As will be apparent to those skilled in the art of statistical analysis, various methods may be applied to determine the best-fit model. In a possible embodiment, the minimization of the mean square error between the measured and the expected statistical distributions may be used. More generally, it is possible to minimize a n-norm distance, such as the Euclidean distance or the l-norm distance. As will be apparent to those skilled in the art of bioinformatics, other statistical fitting methods may be used to determine the best-fit model, such as for instance some of the methods mentioned in US patent application 2014/0052381 by Utirametur et al.

Figure 5:
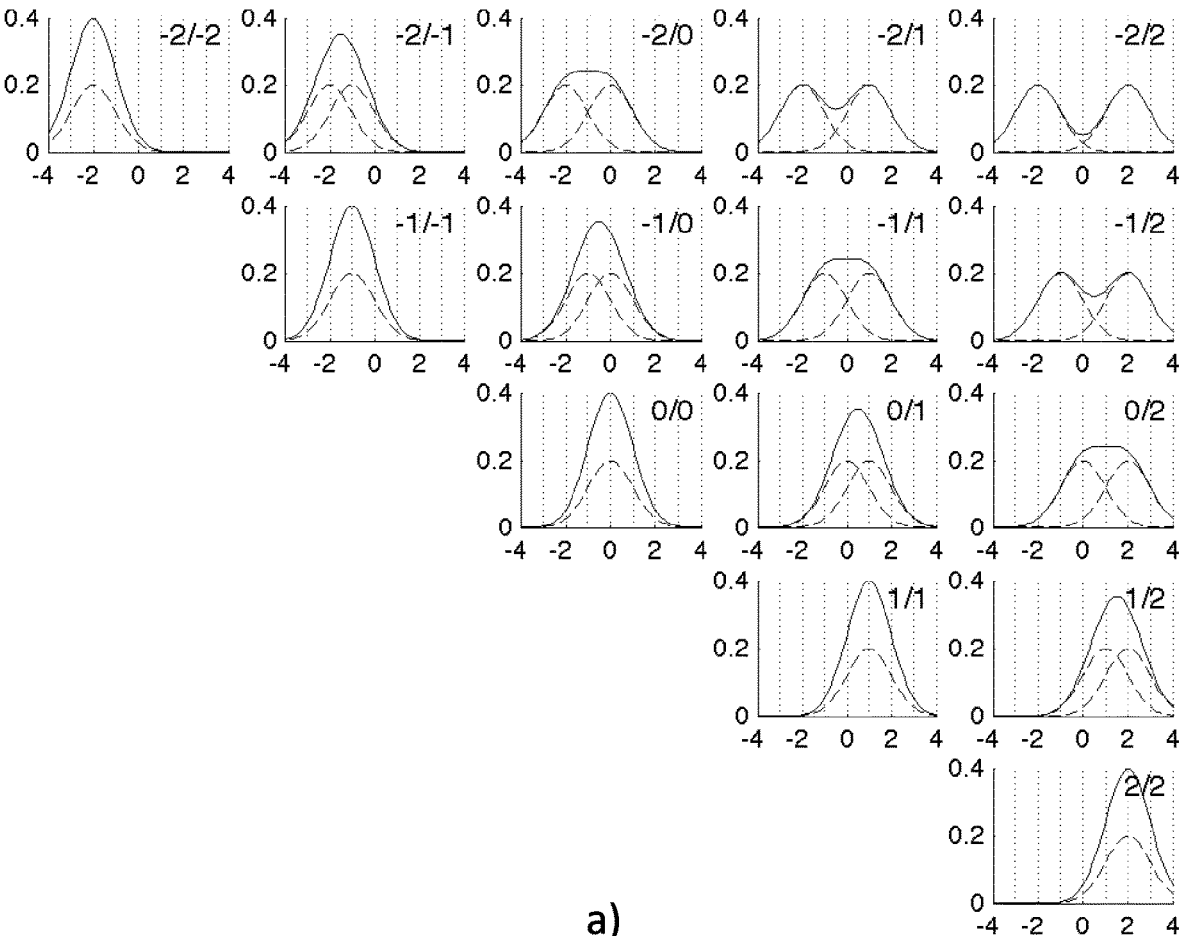
FIG. 5a) shows the graphical representation of all possible expected probability distributions of the relative length of repeat patterns for various deletion and insertion scenarios as may be derived from the probability distribution of the relative length in control data with no mutation but subject to experiment error biases, and FIG. 5b) shows the graphical representation of a measured probability distribution for patient data, to be matched to the closest expected probability distribution scenario.
Figure 5:
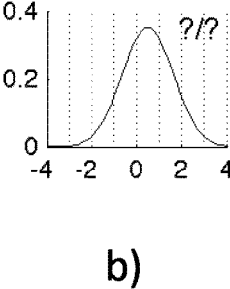

In the FIG. 5 illustrative example (using relative length coordinates) the [0/1] variant scenario will be selected accordingly as the best-fit model for the repeat pattern genomic variant relative to the human genome reference (heterozygous single insertion, for instance 13-A on one allele and 14-A on the other allele, in the CHEK2 [13A/14A] example).

The above proposed methods enable to reliably estimate the unbiased respective probability distributions of the lengths of the repeat pattern (for instance, the repeat of the C homopolymer or the TG heteropolymer basic motif) in the patient sample data when experimental control data coverage is available representing the wild type experimental measurement bias, that is when a control data sample is included in the laboratory pool. However, not all genomic analysis setups provide such a control wild type data. It is therefore necessary to further consider different hypotheses on which actual sample(s) may represent the wild type ("reference") data in the patient pool. This will be better understood with the illustrations of FIG. 6, FIG. 7 and FIG. 8 which plot examples of such hypotheses in the simplest case of comparing 2 samples, respectively of patient 1 and patient 2, to each other in an attempt to determine if one of them corresponds to the wild type sample, possibly with measurement bias misidentifying a mutation in the repeat pattern (the wild type sample variant should be called as [0|0] after refined variant calling 244, regardless of the initial biased observation).

Figure 6:
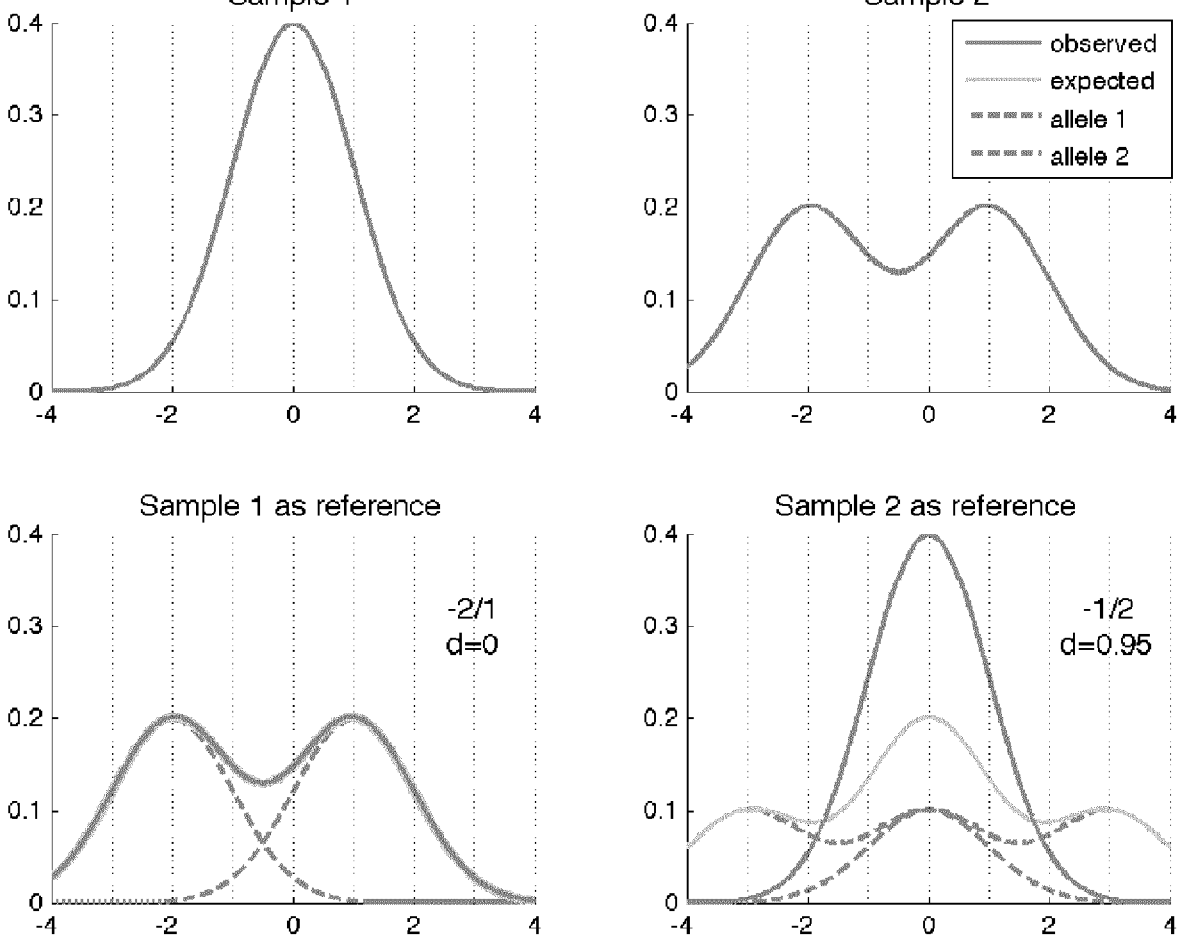
FIG. 6 shows an example of measured probability distributions of the length of repeat patterns for a pair of samples 1 and 2, as well as the expected probability distributions of the length of repeat patterns for each sample relative to the other assumed as the reference.

In FIG. 6, the measured distribution of the relative repeat pattern length of sample 1 is unimodal centered on 0 (no mutation) while the measured distribution of the relative repeat pattern length of sample 2 is bimodal with two peaks respectively at −2 (two deletions) and +1 (one insertion). In the hypothesis that the measured distribution for sample 1 corresponds to the wild type measurement with experimental bias, a perfect match can be found as the minimal possible distance d=0 between the measured distribution for sample 2 and the predicted distribution for a variant model [−2|1] of 2 deletions on one allele and 1 insertion on one allele for sample 2 relative to sample 1. In the hypothesis that the measured distribution for sample 2 corresponds to the wild type measurement with experimental bias, no match can be found (d=0.95) between the measured distribution for sample 1 and the predicted distribution for a variant model [−1|2] of 1 deletion on one allele and 2 deletions one allele for sample 1 relative to sample 2. In this example, the variant calling method 244 enables the genomic data analyzer 120 to identify with good confidence that the repeat pattern length is the same as in the human reference genome for patient 1 on both alleles, corresponding to the wild type (e.g. 13 A nucleotides on CHEK2, 11 T nucleotides on RAD54L, 19 T on ATM, or 11 TG on CFTR) while for patient 2 the repeat pattern length is shorter by two nucleotides on one allele (e.g. 11 A nucleotides on CHEK2, 9 T nucleotides on RAD54L, 17 T on ATM, or 9 TG on CFTR) and longer by one nucleotide compared to the human reference genome on the other allele (e.g. 14 A nucleotides on CHEK2, 12 T nucleotides on RAD54L, 20 T on ATM, or 12 TG on CFTR).

Figure 7:
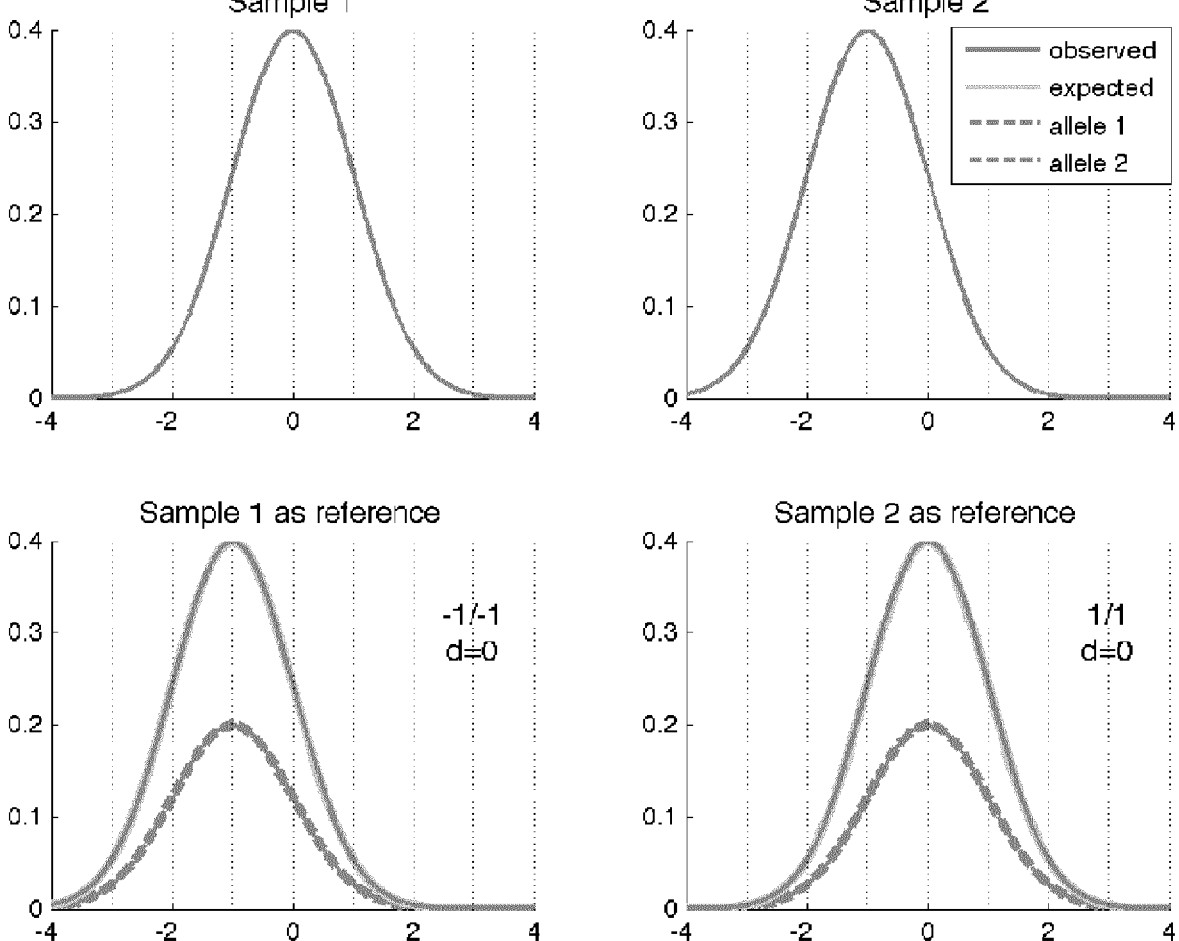
FIG. 7 shows another example of measured probability distributions of the length of repeat patterns for a pair of samples 1 and 2, as well as the expected probability distributions of the length of repeat patterns for each sample relative to the other assumed as the reference.

In FIG. 7, the measured distribution of the relative repeat pattern length of sample 1 is unimodal centered on 0 (no mutation) while the measured distribution of the relative repeat pattern length of sample 2 is unimodal centered at −1 (one homozygous deletion). In the hypothesis that the measured distribution for sample 1 corresponds to the wild type measurement without experimental bias (as it is centered on 0), a perfect match can be found as the minimal possible distance d=0 between the measured distribution for sample 2 and the predicted distribution for a variant model [−1|−1] of a single nucleotide homozygous deletion for sample 2 relative to sample 1. In the hypothesis that the measured distribution for sample 2 corresponds to the wild type measurement with experimental bias of a homozygous deletion (as it is centered on −1), a perfect match can also be found as the minimal possible distance d=0 between the measured distribution for sample 1 and the predicted distribution for a variant model [+1|+1] of a single nucleotide homozygous insertion for sample 1 relative to sample 2. In this example, it is not possible to discriminate whether sample 1 or sample 2 corresponds to the wild type, to further cross-analysis with other samples will be needed for the variant calling method 244 to enable the genomic data analyzer 120 to identify actual variants with good confidence on sample 1 and sample 2.

Figure 8:
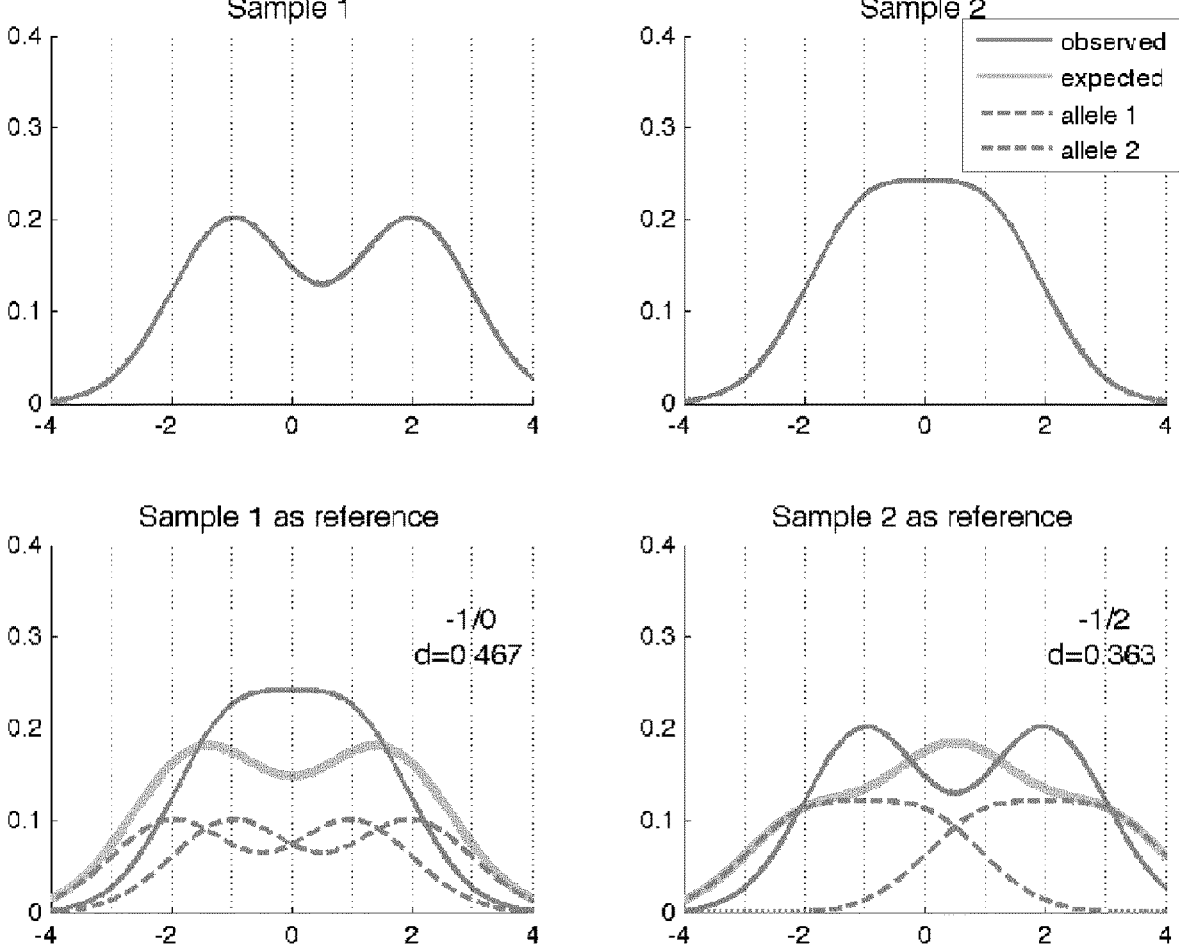
FIG. 8 shows another example of measured probability distributions of the length of repeat patterns for a pair of samples 1 and 2, as well as the expected probability distributions of the length of repeat patterns for each sample relative to the other assumed as the reference.

In FIG. 8, the measured distribution of the relative repeat pattern length of sample 1 is bimodal with two peaks respectively at −1 (one deletion) and +2 (two insertions) while the measured distribution of the relative repeat pattern length of sample 2 is unimodal centered between −1 (one deletion) and +1 (one insertion). In the hypothesis that the measured distribution for sample 1 corresponds to the wild type measurement with experimental bias, the best match can be found at a distance d=0.467 between the measured distribution for sample 2 and the predicted distribution for a variant model [−1|0] of a single nucleotide heterozygous deletion for sample 2 relative to sample 1. In the hypothesis that the measured distribution for sample 2 corresponds to the wild type measurement with experimental bias, the best match can be found at the minimal possible distance d=0.363 between the measured distribution for sample 1 and the predicted distribution for a variant model [−1|+2] of a single nucleotide deletion on one allele and a double nucleotide insertion on the second allele for sample 1 relative to sample 2. In this example, regardless of which sample corresponds to the wild type, we observe that the variant calling method 244 does not enable the genomic data analyzer 120 to identify with enough confidence the repeat pattern length for patient 1 and patient 2. However, it may still be possible to identify it by cross-analyzing more patient samples, as will now be described in further details.

Multi-Sample Cross-Analysis

Figure 9:
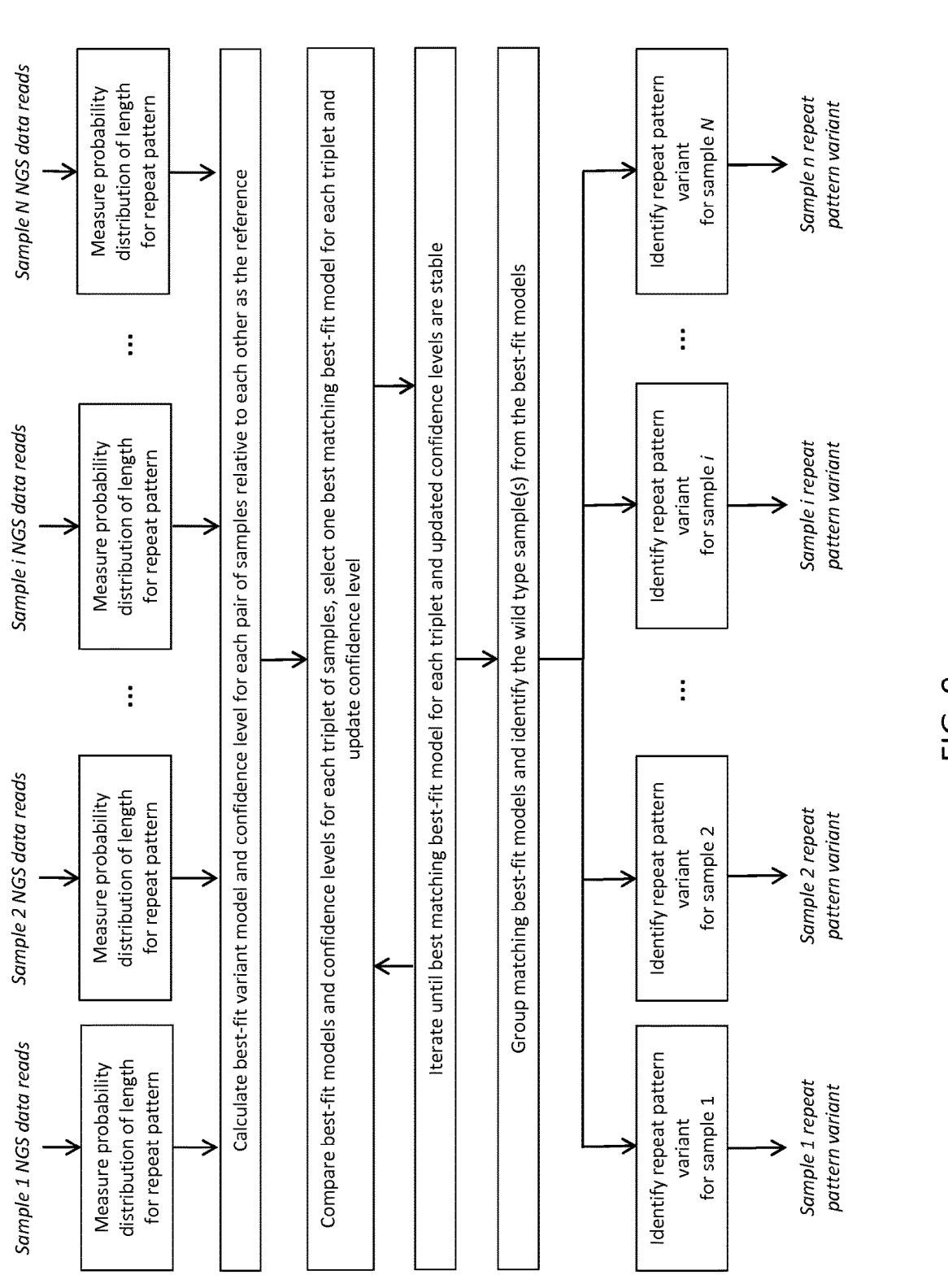
FIG. 9 illustrates a possible overall flow chart of a refined variant calling method according to the present disclosure, which enables to accurately identify repeat pattern variants with increased sensitivity and specificity.

As illustrated by the workflow of FIG. 9, the general approach proposed herein consists in successively considering each sample in the pool of samples as possibly the wild type (WT) reference sample as the working hypothesis. The method may start by calculating the best-fit model with a confidence level for each pair of samples as described in the former section. As formerly illustrated by the examples of FIG. 6, FIG. 7 and FIG. 8, the analysis of each pair of samples may provide a best-fit model with a certain level of confidence. Once sample-to-sample best fit models have been initially identified, further sample cross analysis may proceed with each possible triplet to identify the best matching best-fit model for them as well as a corresponding confidence level. The overall confidence level for each working hypothesis may be iteratively calculated as a function of the distances between the measured distributions of the lengths of the repeat patterns and the matching best-fit variant models as they get refined in each cross-analysis iteration. Different algorithms may be designed to cross-analyze multiple samples under the above assumptions, so that they will converge after a limited number of iterations. Then, identifying the samples corresponding to the wild type (which should be identified by the refined variant calling method 244 as homozygous, no mutation) enables to take into account a possible experimental bias in the pool measurements (which may result in the erroneous detection of mutations when applying non-refined variant calling to the measured data on the repeat patterns genomic regions).

In a pool of samples, there may be several samples carrying the wild type pattern. After cross-analyzing the samples, it is therefore advantageous to try and group them. Certain heuristics may then apply to identify which group is most likely to correspond to the wild type; for instance:

Samples with homozygous variants are more likely to be the wild type samples than those with heterozygous variants, as most experimental biases should apply indifferently to both alleles.

Samples with multiple deletion variants may be the wild type samples (as may be due to the next generation sequencer skipping nucleotides), yet after refined variant calling 244 according to this hypothesis all the other samples should still have variants in the known possible range (e.g., for CFTR, no more than 2 deletions of the TG pattern compared to the human genome reference). In other words, this working assumption can only be considered if the other samples have enough observed pattern length to best-fit a plausible variant model to them.

By identifying the group of samples corresponding to the wild type in the pool of samples based on cross-sample statistical analysis, the refined variant calling method 244 may thus more accurately characterize the repeat pattern variant for each sample in the pool as the variant derived from the wild type bias working hypothesis with the highest confidence level. The proposed genomic data analyzer 120 will therefore detect 244 and report 250 more accurately the repeat pattern variants for multiple patient samples.

In a possible embodiment, the refined variant calling method 244 for identifying a repeat pattern variant as the repeat pattern of at least two nucleotides (homopolymer case) or at least two groups of nucleotides (heteropolymer case: dinucleotide, triplet of nucleotides, etc. . . . ) in the genomic sequence of a patient sample may thus comprise:

(a) identifying a reference repeat pattern $P_{ref}=N*l$ as the repeat of l (l>=2) genomic patterns N in a genomic region of a human genome reference sequence;

(b) obtaining, with a next generation sequencer, n patient sets of next generation sequencing data reads covering the reference repeat pattern genomic region S= $\{S_1, S_2, \ldots, S_i, \ldots, S_n\}$ from a pool of n enriched genomic patient samples, each set $S_i$ being associated with a patient sample, the number n of enriched genomic patient samples being at least 4;

(c) for each patient sample i in the set S of patient samples, measuring the distribution $P_i$ of the length of the repeat pattern in the set of next generation sequencing reads $S_i$;

(d) for a possible pair of patient samples i and j, j>i:

(d1) estimating for sample j, under the assumption that sample i carries the wild type human genome reference homopolymer pattern $P_{ref}=N*l$ for each allele, a best-fit model $$[V_{j|i}^1|V_{j|i}^2]$$

of the two allele variants for sample j, with a confidence level $L_{j|i}$, as well as the smallest distance $D_{j|i}$ between the measured distribution $P_j$ for sample j and the predicted unimodal or bimodal distribution for the best-fit variant model $$[V_{j|i}^1|V_{j|i}^2];$$

(d2) estimating for sample i, under the assumption that sample j carries the wild type human genome reference homopolymer pattern $P_{ref}=N*l$ for each allele, a best-fit model $$[V_{i|j}^1|V_{i|j}^2]$$

of the two allele variants for sample i, with a confidence level $L_{i|j}$, as well as the smallest distance $D_{i|j}$ between the measured distribution $P_i$ for sample i and the predicted unimodal or bimodal distribution for the best fit variant model $$[V_{i|j}^1|V_{i|j}^2];$$

(d3) if $D_{i|j} \geq D_{j|i}$ selecting for the pair of samples (i,j) the best-fit model $$[V_{ij}^1|V_{ij}^2] = [-V_{j|i}^1|-V_{j|i}^2]$$

as the best-fit variant model of the two allele variants and the confidence level $L_{ij}=L_{j|i}$ as the confidence level value for this best-fit match with sample i as the reference sample of pair (i,j);

(d4) else if $D_{i|j} < D_{j|i}$ selecting for the pair of samples (i,j) the model $$[V_{ij}^1|V_{ij}^2] = [V_{i|j}^1|V_{i|j}^2]$$

as the best-fit variant model of the two allele variants and the confidence level $L_{ij}=L_{i|j}$ as the confidence level value for this best-fit match with sample j as the reference sample of pair (i,j);

(e) for each possible triplet of patient samples i, j>i, k>j, comparing their respective best-fit models $$[V_{ij}^1|V_{ij}^2], [V_{jk}^1|V_{jk}^2], [V_{ik}^1|V_{ik}^2]$$

and:

(e1) if all three best-fit models for the triplet of patient samples match each other, increasing their confidence levels $L_{ij}$, $L_{jk}$, $L_{ik}$;

(e2) else the three best-fit models do not match each other, replacing the best-fit model with the lowest confidence level out of the subset by a best-fit model calculated from the other two samples of the subset, and decreasing the confidence levels $L_{ij}$, $L_{jk}$, $L_{ik}$ of all the best-fit models for the triplet of patient samples.

(f) repeating step (e) until the results are no longer varying;

(g) matching groups of identical best-fit variant models and identifying the most likely group carrying the wild type variant;

(h) for each sample out of the group carrying the wild type variant, unbiasing the best-fit variant model of the group comprising this sample as a function of the best-fit variant model for the identified wild type group, and reporting the unbiased variant for the sample.

As will be apparent to those skilled in the art of statistics, the confidence level may be initially estimated and further refined by different mathematical methods. In a possible embodiment, for any pair of patient samples i and j, j>i, the confidence level $L_{ij}$ of the estimation $$[V_{ij}^1|V_{ij}^2]$$

may be initially calculated as:

$$L_{ij} = \begin{cases} 1 - D_{i|j}/D_{i|j}', & D_{i|j} > D_{j|i} \\ 1 - D_{j|i}/D_{j|i}', & D_{i|j} \leq D_{j|i} \end{cases}$$

where $D_{j|i}$ is the smallest distance and $P_{j|i}'$ is the second smallest distance as calculated in step d1), and $D_{i|j}$ is the smallest distance and $D_{i|j}'$ is the second smallest distance as calculated in step d2). The $L_{ij}$ confidence level value is thus a floating value in the range [0,1], with value 1 quantifying a maximal confidence level for either i or j as the reference and value 0 quantifying a minimal confidence level for instance when it is not possible to differentiate i from j as the reference.

In a possible embodiment, the confidence levels for each pair in a triplet subset i, j, k of matching best-fit models may be respectively increased in step e1) as:

$$L_{ij}'=1-(1-L_{ij})(1-L_{jk}*L_{ik})$$

$$L_{jk}'=1-(1-L_{ij})(1-L_{ij}*L_{ik})$$

$$L_{ik}'=1-(1-L_{ik})(1-L_{ij}*L_{ik})$$

In a possible embodiment, the confidence levels for each pair in a triplet subset i, j, k of non-matching best-fit models where the lowest initial confidence level is $L_{ik}$ may be respectively decreased in step e2) as:

$$L_{ij}'=L_{ij}-(1-L_{jk})*L_{ik}$$

$$L_{jk}'=L_{jk}-(1-L_{ij})*L_{ik}$$

$$L_{ik}'=\max(0,L_{ij}/L_{jk}-L_{ik})$$

and the best-fit model for the pair j,k with the lowest confidence level out of the subset may be replaced by a best-fit model calculated from the other two samples of the subset j by assuming inter-sample transitivity within the triplet, as:

$$\left[V_{ik}^{1\prime}|V_{ik}^{2\prime}\right] = \left[V_{ij}^1 + V_{ij}^1|V_{jk}^2 + V_{jk}^2\right]$$

In particular, when different types of heterozygous mutations cannot be compared, the result of $$\left[V_{ij,k}^1|V_{ij,k}^2\right]$$

may be excluded from the cross-analysis ([NA|NA]):
  1. if $$V_{ik}^1 \neq V_{ik}^2$$

(indicating a heterozygous mutation in either sample i or sample k) and $D_{ilk} > D_{kli}$ (indicating that sample k is homozygous) and $$V_{kj}^1 \neq V_{kj}^2$$

(indicating a heterozygous mutation in either sample j or sample k) and $D_{jlk} > D_{klj}$ (indicating that sample k is homozygous) and $$\left[V_{ik}^1 \neq -V_{kj}^1 \text{ or } V_{ik}^2 \neq -V_{kj}^2\right]$$

(indicating not the same type of heterozygous mutation in sample i and sample k);
  2. if $$\left[V_{ik}^1|V_{ik}^2\right]$$

equals to [NA|NA] or $$\left[V_{kj}^1|V_{kj}^2\right]$$

equals to [NA|NA].
  In another particular case, if $$\left[V_{ij}^1|V_{ij}^2\right]$$

equals to [NA|NA]: as this result can be because of the sequencing noise in sample i or sample j, the result can be re-measured with the same formula above, from the other two samples of a triplet.
  The corresponding confidence level for $$\left[V_{ij,k}^1|V_{ij,k}^2\right]$$

may otherwise be estimated as:

$$L_{ij,k} = L_{ik} * L_{kj}$$

For each pair i and j, at most n−2 results of $$\left[V_{ij,k}^1|V_{ij,k}^2\right]$$

and $L_{ij,k}$ values may thus be derived from triplets, where n is the number of patient samples. Moreover, starting from $$\left[V_{ij,0}^1|V_{ij,0}^2\right] = \left[V_{ij}^1|V_{ij}^2\right]$$

and $L_{ij,0} = L_{ij}$, for each pair i and j, there are at most n−1 results of $$\left[V_{ij,k}^1|V_{ij,k}^2\right]$$

and $L_{ij,k}$, with k=0 to n, k≠i and k≠j.
  The above steps a) to f) enable to identify the most likely best-fit variant models from cross-analyzing the data out from the pool of samples. An example application of the above proposed cross-sample comparison methods will now be described as illustrated in FIG. 10 to FIG. 13.
  In FIG. 10, sample i=1 vs sample j=2 is associated with the best-fit variant model of no mutation relative to each other $$\left[V_{12}^1|V_{12}^2\right] = [0|0],$$

with a confidence level $L_{12}$=0.46; sample i=1 vs sample j=3 is associated with the best-fit variant model of no mutation relative to each other $$\left[V_{13}^1|V_{13}^2\right] = [0|0],$$

with a confidence level $L_{13}$=0.60; sample i=2 vs sample j=3 is associated with the best-fit variant model of no mutation relative to each other $$\left[V_{23}^1|V_{23}^2\right] = [0|0],$$

with a confidence level $L_{23}$=0.32. The best-fit models for the triplet of patient samples (1,2,3) match each other thus the corresponding confidence levels $L_{12}$, $L_{13}$, $L_{23}$ may be increased accordingly as $L_{12}$ '=0.564, $L_{23}$ '=0.518 and $L_{13}$'=0.659 respectively.
  In FIG. 11, sample i=2 vs sample j=7 is associated with the best-fit variant model of no mutation relative to each other $$\left[V_{27}^1|V_{27}^2\right] = = [0|0],$$

with a confidence level $L_{27}$=0.18; sample i=2 vs sample j=8 is associated with the best-fit variant model of one heterozygous deletion in sample 2 relative to sample 8

$$[V_{28}^1 | V_{28}^2] == [-1|0],$$

with a confidence level $L_{28}=0.10$; sample $i=7$ vs sample $j=8$ is associated with the best-fit variant model of no mutation relative to each other $$[V_{78}^1 | V_{78}^2] = [0|0],$$

with a confidence level $L_{78}=0.68$. The best-fit models for the subset of cross-samples 2 vs 7 and 7 vs 8 and 2 vs 8 do not match each other and confidence level $L_{28}=0.10$ is the lowest value in the triplet, thus the best-fit model $$[V_{28}^1 | V_{28}^2]$$

of sample 2 vs sample 8 may be replaced by that of the matching subset $$[V_{27}^1 + V_{78}^1 | V_{27}^2 + V_{78}^2] = [0|0],$$

and the corresponding confidence levels $L_{27}$, $L_{28}$, $L_{78}$ shall be decreased accordingly as $L_{27}'=0.148$, $L_{78}'=0.598$ and $L_{28}'=0.022$ respectively.

In FIG. 12, sample $i=1$ vs sample $j=2$ is associated with the best-fit variant model of no mutation relative to each other $$[V_{12}^1 | V_{12}^2] = [0|0],$$

with a confidence level $L_{12}=0.46$; sample $i=1$ vs sample $j=6$ is associated with the best-fit variant model of no mutation relative to each other $$[V_{16}^1 | V_{16}^2] = [0|0],$$

with a confidence level $L_{16}=0.67$; but sample $i=2$ vs sample $j=6$ has been classified as unreliable (NA) in a former step. The best-fit model $$[V_{26}^1 | V_{26}^2]$$

of sample 2 vs sample 6 may be replaced by that of the matching subset $$[V_{21}^1 + V_{16}^1 | V_{21}^2 + V_{16}^2] = [0|0],$$

with a confidence level $L_{26.1}=0.308$. The confidence level $L_{12}$ and $L_{16}$ remain unchanged, as [NA|NA] between sample 2 and sample 6 does not contribute any information to the triplet.

FIG. 13 represents an exemplary table of the most likely best-fit variant models and their corresponding corrected confidence levels to which values the proposed method has converged after 4 iterations. The number of iterations may vary with the quality of the input data and the number of samples in the pool, but in general a few iterations are enough for the method to converge to consistent results in a pool.

More generally, the best-fit models out of step (f) may be grouped together into q different groups of samples ($1 \leq q \leq n-1$) based on $$[V_{ij,k}^1 | V_{ij,k}^2]$$

values such that within each group of samples $G_r$ ($1 \leq r \leq q$), all the results agree with each other. Samples with the result [NA|NA] are thus not considered in this step. The overall confidence level for this group may then be calculated as:

$$L_{ij.Gr} = 1 - \prod\nolimits_{k \in G_r} (1 - L_{ij.k})$$

For example, if group 1 contains 3 samples with cross-analysis confidence levels 0.5, 0.4 and 0.3 respectively, then $L_{ij.G1}=1-(1-0.5)(1-0.4)(1-0.3)=0.79$.

If there are more than 1 group (q>1) out of step e), we may choose the group $G_h$ with the highest confidence level $L_{ij.Gh}$, and set the value $$[V_{ij.Gh}^1 | V_{ij.Gh}^2]$$

of this group as the new value at iteration p for $$[V_{ij.Gh}^1 | V_{ij.Gh}^2]$$

before the $p^{th}$ iteration in step f).

The new confidence level for pair i and j may then be calculated as increased or decreased as:

$$L_{ij.new} = \max\left(0, 1\text{-}(1\text{-}L_{ij.Gh}) * \prod\nolimits_{1 \leq r \leq q, r \neq h} (1 - L_{ij.Gr})^{-1}\right)$$

For example, if there are 3 groups $G_1$, $G_2$, $G_3$ with confidence level 0.9, 0.8, 0.7 correspondingly: as group $G_1$ has the highest confidence level 0.9, we set $$[V_{ij.G1}^1 | V_{ij.G1}^2]$$

as the new result for $$[V_{ij.p}^1 | V_{ij.p}^2].$$

And the new confidence level may be:

$$L_{ij.p}=\max(0,1-(1-0.9)(1-0.8)^{-1}(1-0.7)^{-1})=\max(0,-0.67)=0.$$

By all the steps above by the iteration step f) all cross-sample best-fit models $$[V_{ij}^1|V_{ij}^2]$$

and the corresponding matching level $L_{ij}$ may be updated to new results for all sample pairs i and j. Then, if there is more than 1 group (q>1) for any pair i and j (which means the results has conflicts), the whole iteration shall be repeated, while if all i and j pairs generate only 1 group (which means all results agree with each other, reaching a stable value), the iteration may be stopped in step f).

Selection of the Most Likely Group of Samples Corresponding to the Wild Type

In order to un-bias the data for all samples, it is necessary to identify which subset of the identified groups of best-fit variant models correspond to the wild type reference, that do not carry any mutations but may have been biased solely by the next generation sequencing workflow processes. In the example of FIG. 13, all converged models match each other as [0|0], that is no mutation relative to each other, so it can be easily derived that all samples are the same wild type reference (no variant mutation identified to report). In the example of FIG. 14 however, the best-fit variant models after cross-analysis iteration can be matched in two groups of samples, namely group 1={S1, S3, S4, S5, S6, S7, S8} and group 3={S2}. In the latter case there is a need to identify which group most likely carries the wild type.

In a possible embodiment, the refined variant calling method 244 and genomic data analyzer 120 for detecting and characterizing a repeat pattern variant in the genomic sequence of a patient sample may comprise identifying the subset of one or more samples corresponding to the wild type reference in the pool of patient samples by selecting as the wild type the homozygous best-fit variant model group $[V_G|V_G]$ with which the largest number of samples i,j, . . . have been associated out of cross-analyzing the pool of samples.

More generally, the refined variant calling method 244 and genomic data analyzer 120 for detecting and reporting 250 a homopolymer variant as the repeat pattern of at least two nucleotides in the genomic sequence of a patient sample may comprise identifying the subset of one or more samples corresponding to the wild type reference in the pool of patient samples by selecting as the wild type the homozygous best-fit variant model $[V_G|V_G]$ for which additional hypotheses have been met.

For instance, if group G is associated with the wild type reference and $V_G=-1$, the refined variant calling method 244 and genomic data analyzer 120 may identify the repeat pattern variants in the sample of group G as those corresponding to the human genome reference (relative length [0|0]), regardless of the actually measured homopolymer length best-fit model for group G [−1|−1] in the next generation sequencing reads, which may for instance have been initially measured shorter due to sequencing errors.

In the example of FIG. 14, only one group (group 1) is associated with a homozygous best-fit variant model. This group will therefore be identified as matching the wild type, here without observation bias ([0|0] best-fit variant model). In the other group 2, a single sample 2 will be characterized by the refined variant calling method 244 and reported 250 by the genomic data analyzer 120 as carrying a heterozygous insertion relative to the human genome reference ([0|1] best-fit variant model relative to unbiased wild type variant model [0|0]).

Figure 15:
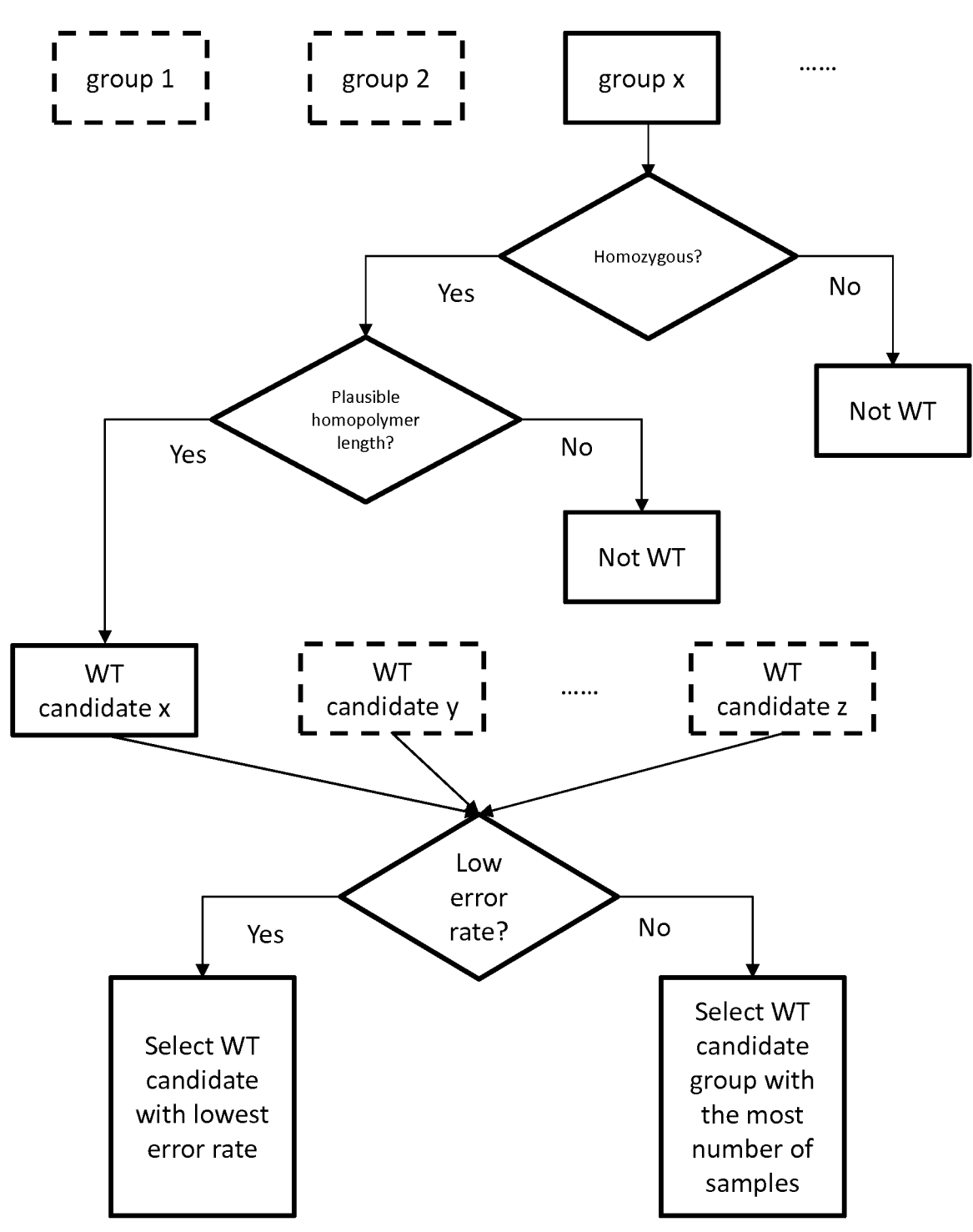
FIG. 15 illustrates the logical flow chart of the proposed method to identify group of samples corresponding to the wild type human genome reference in the pool of samples.

In a possible embodiment, when there are more than two wild type group candidates after sorting the according to their homozygous status and/or their size, further hypotheses may be considered to ensure that the result is as statistically robust as possible. For instance, all the variants identified in the pool of samples should be biologically possible. Therefore, in a possible embodiment, the refined variant calling method 244 and genomic data analyzer 120 for detecting a homopolymer variant as the repeat pattern of at least two nucleotides in the genomic sequence of a patient sample may thus further comprise identifying the subset of one or more samples corresponding to the wild type reference in the pool of patient samples by:

(g1) for each possible best-fit variant model $$[V_G^1|V_G^2]$$

identified for a group G of one or more sample pair, identifying if the variant is homozygous $$V_G^1 = V_G^2;$$

otherwise, excluding the best-fit variant model $$[V_G^1|V_G^2]$$

as the wild type reference for the pool of samples;

(g2) for each group G of homozygous best-fit variant model $$[V_G^1|V_G^2],$$

for each other group G' of best-fit variant model $$[V_{G'}^1|V_{G'}^2],$$

verifying if $$[V_{G'}^1|V_{G'}^2]$$

is a possible variant under the hypothesis that the homozygous best-fit variant model $$[V_G^1|V_G^2]$$

is the wild type; for instance, if $$V_{G'}^1 < V_G^1, \text{ and/or } V_{G'}^2, < V_G^2,$$

verifying that the length of the repeat pattern with the $$[V_{G'}^1|V_{G'}^2]$$

best-fit variant model is long enough to be detected as a plausible deletion variant, or if $$V_{G'}^1 > V_G^1 \text{ and/or } V_{G'}^2 > V_G^2$$

verifying that the length of the repeat pattern with the $$[V_{G'}^1|V_{G'}^2]$$

best-fit variant model is short enough to be detected as a plausible insertion variant; otherwise, excluding the best-fit variant model $$[V_G^1|V_G^2],$$

as the wild type reference;
  (g3) for each remaining group of homozygous best-fit variant model $$[V_G^1|V_G^2],$$

estimating an error rate based on the average homopolymer length h and the standard deviation SD in each group:
  If $\bar{h}$ is close enough (within a pre-defined threshold threshold_h, for instance in the range of 0 to 0.1) to the nearest integer $[\bar{h}]$, that is if $abs(\bar{h}-[\bar{h}]) <$ threshold_h, and if SD is small enough to be under a predefined threshold threshold_sd (selected for instance in the range of 0 to 0.1), that is and if SD<threshold_sd, selecting the homozygous best-fit variant model $$[V_G^1|V_G^2]$$

as the wild type reference with low error rate and reporting all samples i,j, . . . associated with this group G as carrying the human genome reference repeat pattern;
  Otherwise, selecting as the wild type the group of homozygous best-fit variant model $$[V_G^1|V_G^2]$$

which comprises the largest number of samples.
  FIG. 15 shows a simplified possible workflow of the above wild type group selection logic as may be applied, with a processor, by the proposed variant calling refinement method 244.
  The proposed genomic data analyzer 120 enables to serve thousands of sourcing laboratories, processing the data from hundreds of thousands of clinical samples processed with multiple enrichment technologies and sequenced on a diversity of next generation sequencing (NGS) platforms. By utilizing this rich data set coupled with the proposed genomic data analysis methods, robust and accurate variant calling results can be reached with the proposed automated workflow sensitivity and specificity matching that of manual algorithm configuration and fine-tuning by bioinformatics experts. Moreover, the proposed fully automated genomic data analyzer 120 system can be deployed, tested and validated without requiring individual setup and fine-tuning of their specific NGS genomic analysis workflow by the sourcing laboratories, and will thus accelerate access to personalized and precision medicine for hundreds of thousands of patients in Europe and worldwide.

Experimental Data

Figure 16:
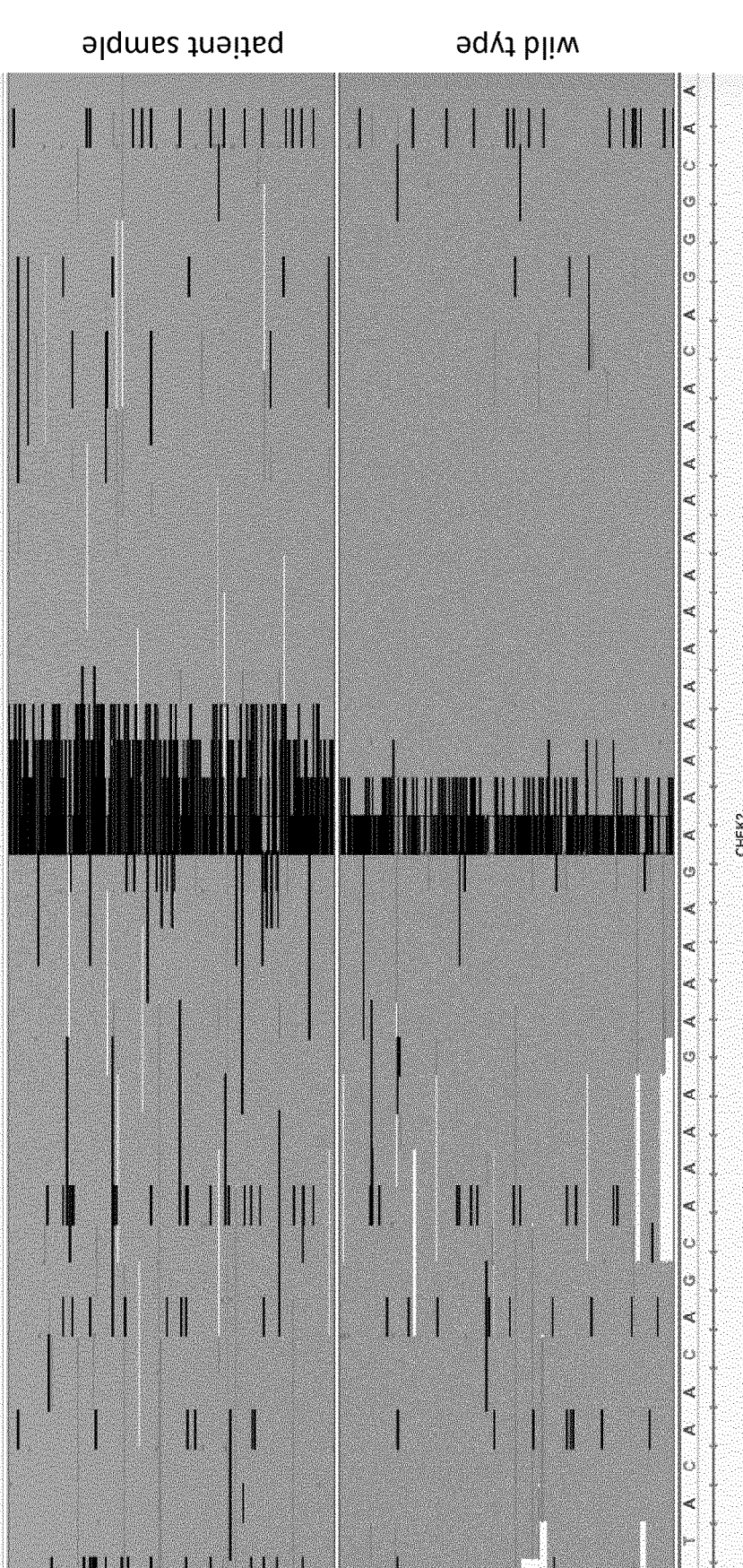
FIG. 16 shows the NGS data coverage for an exemplary repeat homopolymer pattern on the CHEK2 gene from an experiment pool comprising a mixture of mutated patient samples and wild type samples.
Figure 17:
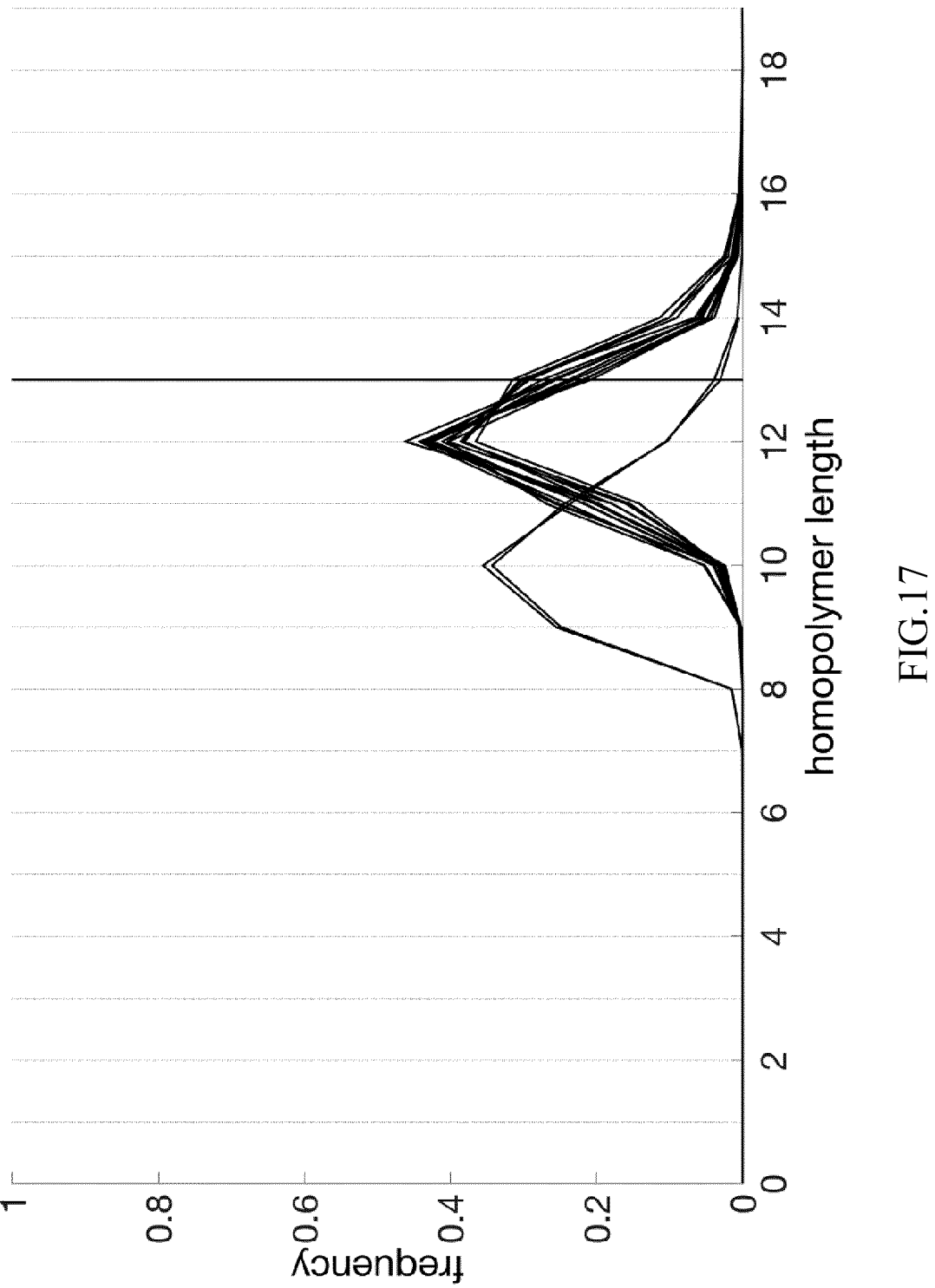
FIG. 17 shows the corresponding measured distribution of the pattern lengths.

The proposed genomic data analyzer 120 has been adapted in the Sophia Genetics Data Driven Medicine (DDM) genomic analysis software platform to implement the proposed method as a supplementary method for improved detection 244 and reporting 250 of homopolymer variants in human genes over the prior art NGS workflows. FIG. 16) shows the NGS data coverage for an exemplary repeat homopolymer pattern on the CHEK2 gene from an experiment pool comprising a mixture of mutated patient samples and wild type samples, and FIG. 17) shows the corresponding measured distribution of the pattern lengths. The sequencing workflow introduces a bias of one deletion so the CHEK2 repeat pattern length for the wild type is centered at 12 repeats instead of 13. The experiment pool also comprises samples centered at 10 repeats. Thanks to the proposed method, the bias is corrected and the genomic data analyzer correctly reports the wild type variants (no mutation) as well as the corrected variants (11 repeats, that is two deletions of the pattern relative to the wild type).

Figure 18:
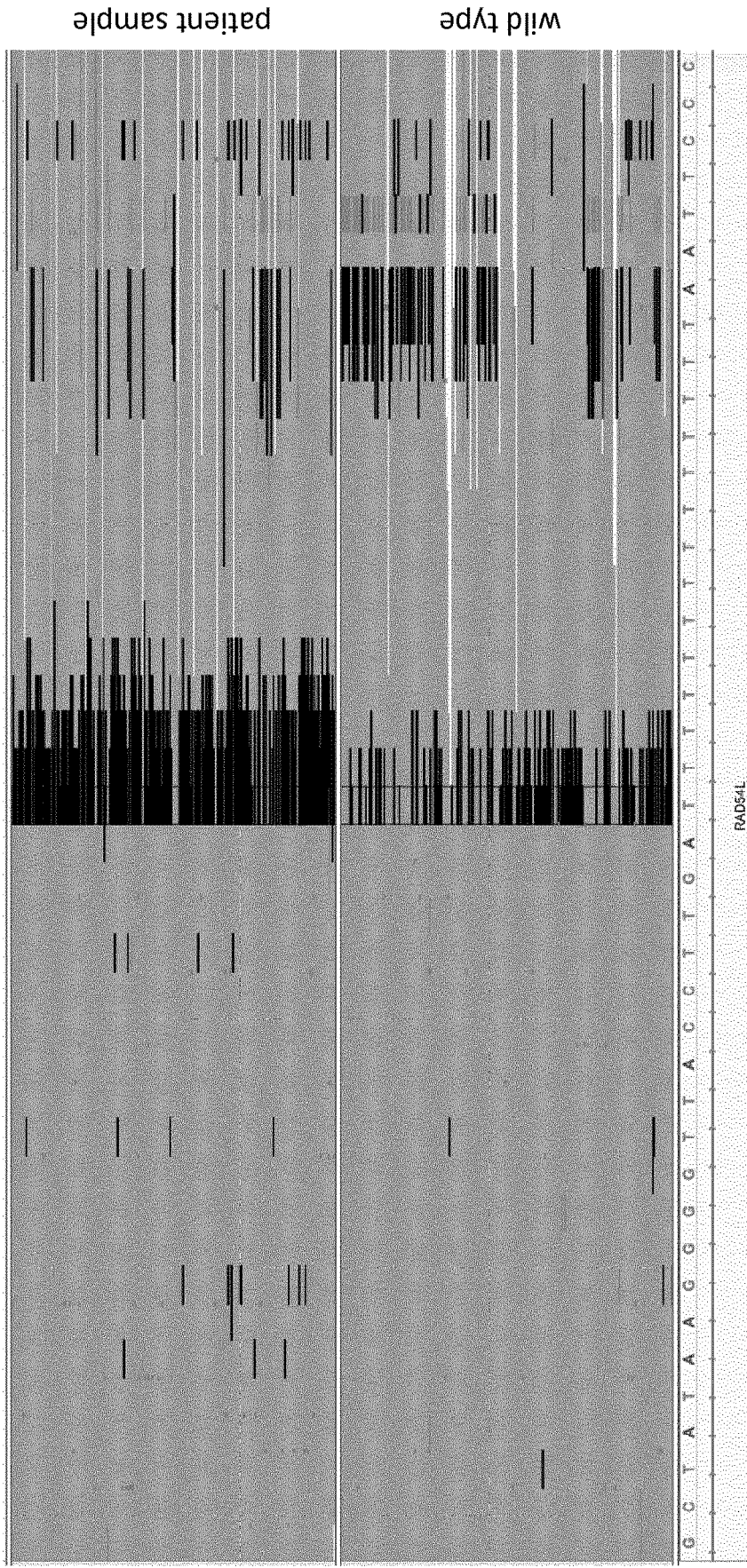
FIG. 18 shows the NGS data coverage for an exemplary repeat homopolymer pattern on the RAD54L gene from an experiment pool comprising a mixture of mutated patient samples and wild type samples.
Figure 19:
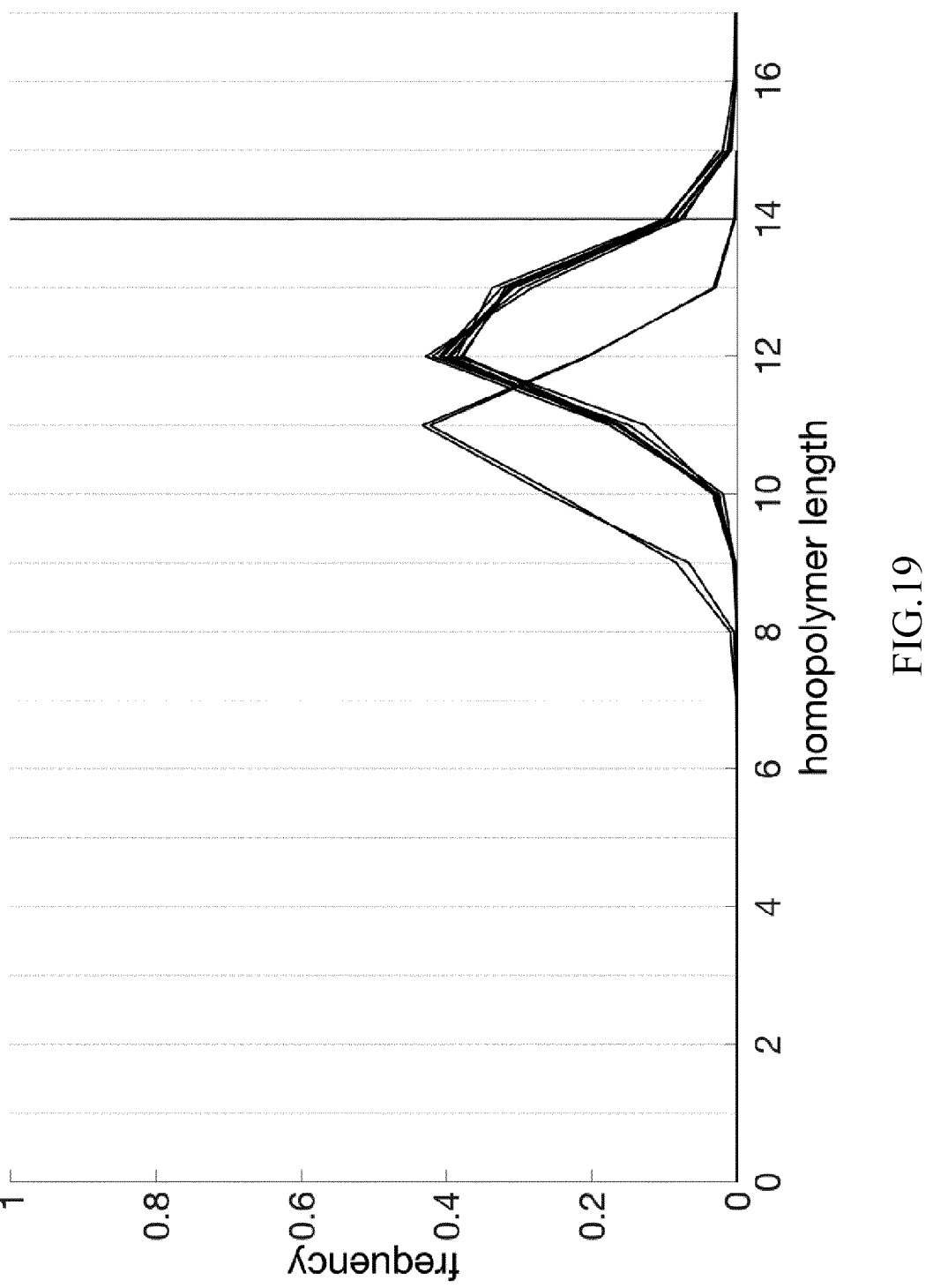
FIG. 19 shows the corresponding measured distribution of the pattern lengths.

FIG. 18) shows the NGS data coverage for an exemplary repeat homopolymer pattern on the RAD54L gene from an experiment pool comprising a mixture of mutated patient samples and wild type samples, and FIG. 19) shows the corresponding measured distribution of the pattern lengths. The sequencing workflow introduces a bias of twos deletion so the RAD54L repeat pattern length for the wild type is centered at 12 repeats instead of 14. The experiment pool also comprises samples centered at 11 repeats. Thanks to the proposed method, the bias is corrected and the genomic data analyzer correctly reports the wild type variants (no mutation) as well as the corrected variants (12 repeats, that is one deletion of the pattern relative to the wild type).

Figure 20:
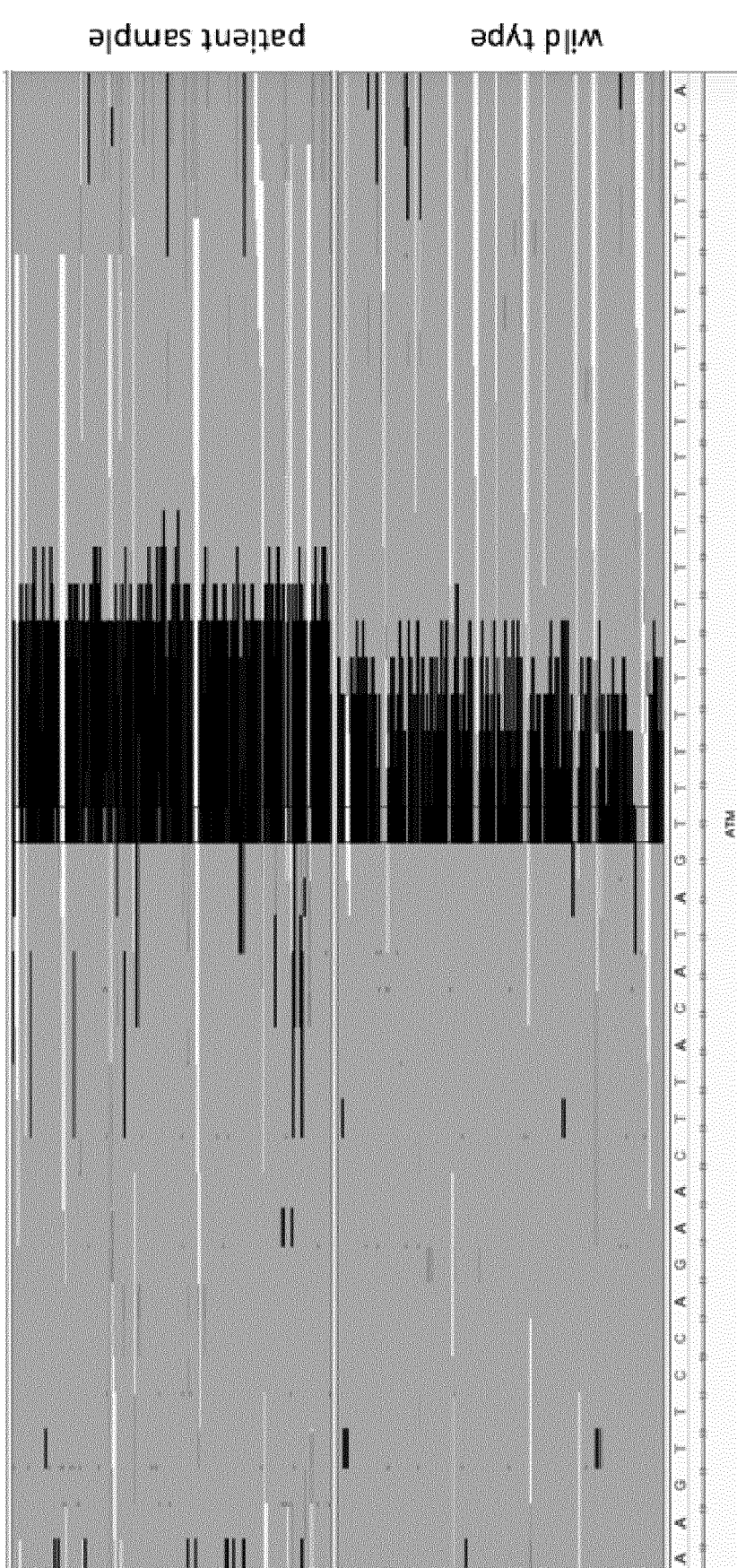
FIG. 20 shows a diagram of the NGS data coverage for an exemplary repeat homopolymer pattern on the ATM gene from an experiment pool comprising a mixture of mutated patient samples and wild type samples.
Figure 21:
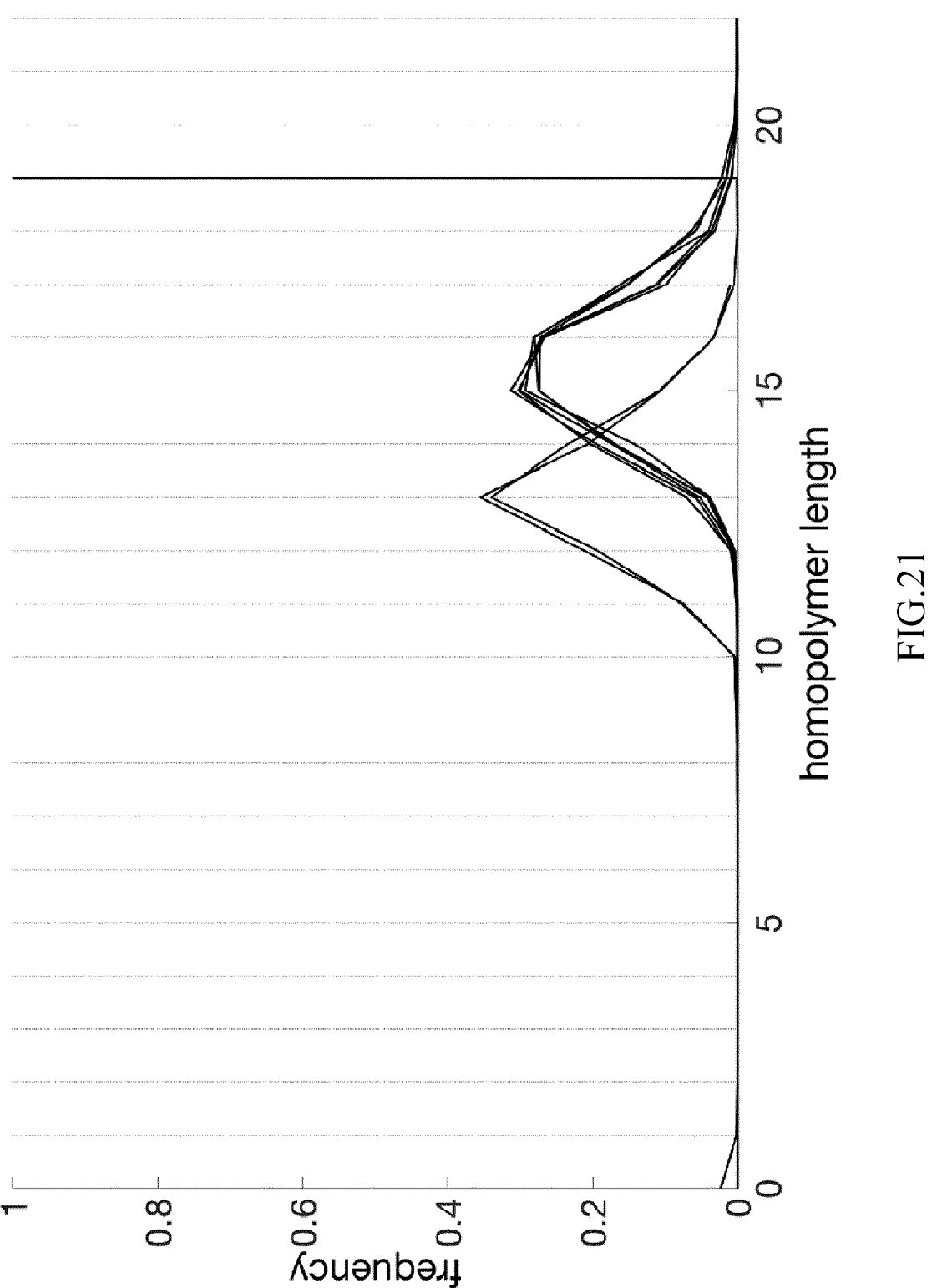
FIG. 21 shows the corresponding measured distribution of the pattern lengths.

FIG. 20) shows a diagram of the NGS data coverage for an exemplary repeat homopolymer pattern on the ATM gene from an experiment pool comprising a mixture of mutated patient samples and wild type samples, and FIG. 21) shows the corresponding measured distribution of the pattern lengths. The sequencing workflow introduces a bias of one deletion so the ATM repeat pattern length for the wild type is centered at 15 repeats instead of 19. The experiment pool also comprises samples centered at 13 repeats. Thanks to the proposed method, the bias is corrected and the genomic data analyzer correctly reports the wild type variants (no mutation) as well as the corrected variants (17 repeats, that is two deletions of the pattern relative to the wild type).

Figure 22:
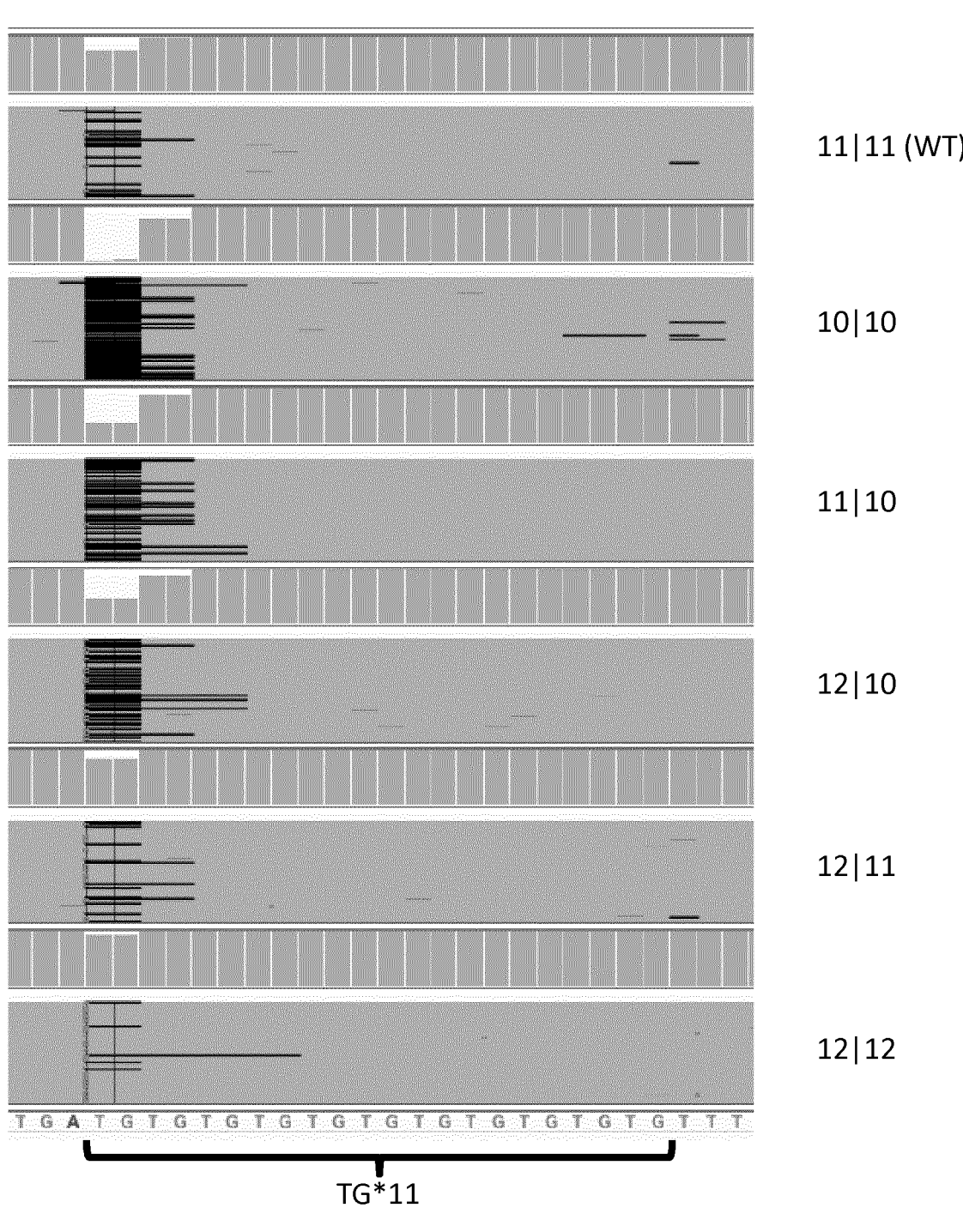
FIG. 22 shows a diagram of the NGS data coverage for an exemplary repeat heteropolymer pattern on the ATM gene from an experiment pool comprising a mixture of patient samples with different mutations.
Figure 23:
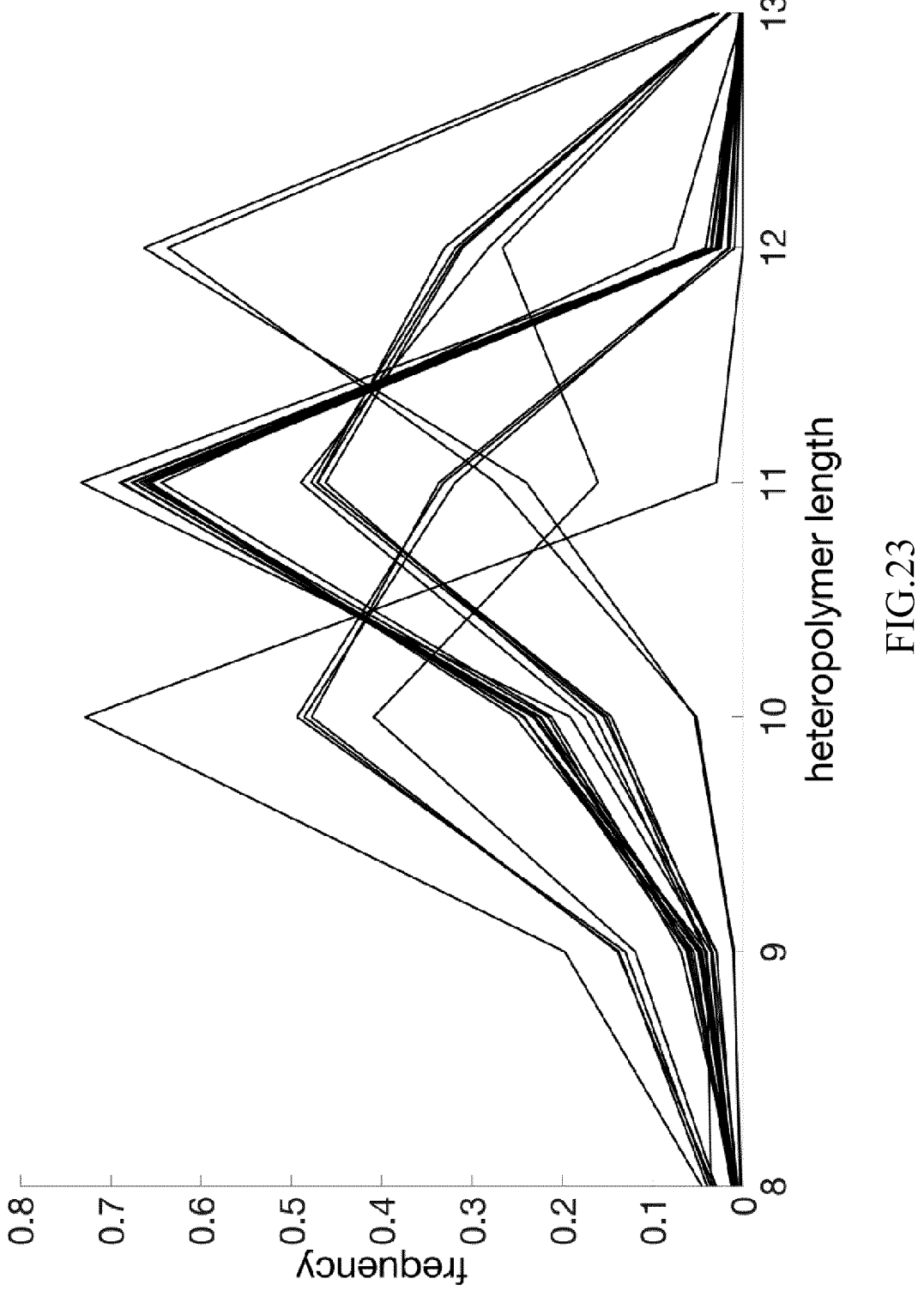
FIG. 23 shows the corresponding measured distribution of the pattern lengths.

FIG. 22) shows a diagram of the NGS data coverage for an exemplary repeat heteropolymer pattern on the CFTR gene from an experiment pool comprising a mixture of patient samples with different mutations, and FIG. 23) shows the corresponding measured distribution of the pattern lengths. The CFTR TG repeat pattern length for the wild type is centered at 11 repeats, same as the reference length in human genome, however the sequencing workflow did introduce a bias of one deletion in about 30% of the sequences, which is similar to a heterozygous deletion. The experiment pool also comprises all combinations of samples that each allele centered between 10 and 12 repeats. Thanks to the proposed method, the bias is corrected and the genomic data analyzer correctly reports the wild type variants (no mutation) as well as all combinations of the variants.

Thus, by optimizing an NGS assay based on a mutation panel with the proposed bioinformatics methods, it is possible to provide improved sensitivity and specificity comparable to the classic methods of Sanger sequencing at a significantly lower cost for genomic analysis. The proposed methods also improve the performance of the prior art NGS workflows in detecting those mutations regardless of the experimental bias introduced by the next generation sequencing platforms. Current applications include diagnostics, neonatal and carrier screening for a diversity of hereditary as well as somatic diseases such as cancer.

Other Embodiments and Applications

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In particular, as will be apparent to those skilled in the art of genomics and personalized medicine, the proposed methods are not limited to the specifics of short nucleotide repeats (homopolymer or heteropolymer) gene constructs as described in certain examples throughout this disclosure. While examples have been described herein for the analysis of the CHEK2, RAD54L, ATM, BRCA and CFTR genes, other areas of medical genomics practice are still on-going research in associating genomic analysis of certain gene regions with certain pathologies. The proposed refined variant calling method 244 may thus apply to improve the variant detection in other genomic regions than these exemplary genes if such regions are characterized by repeat patterns and associated with different diagnoses by future medical research works. This may be the case for instance in the field of neurological diseases where recent development in genome-edited animal models is accelerating the study of multiple mutations, while there are already known associations between certain heteropolymer repeats and certain diseases, such as for instance the CAG polyglutamine (polyQ) repeat variants in Huntington as well as ataxia diseases.

As will be apparent to those skilled in the art of digital data communications, the methods described herein may be indifferently applied to various data structures such as data files or data streams. The terms "data", "data structures", "data fields", "file", or "stream" may thus be used indifferently throughout this specification.

As will be apparent to those skilled in the art statistics, the methods described herein may be indifferently applied to various statistical methods such as probability representations and statistical measurements. The terms "distribution", "likelihood", "probability" may thus be used indifferently throughout this specification. Although the detailed description above contains many specific details, these should not be construed as limiting the scope of the embodiments but as merely providing illustrations of some of several embodiments.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, units, or mechanisms. Modules or units may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors. Similarly, the methods described herein may be at least partially processor-implemented, a processor being an example of hardware. For example, at least some of the operations of a method may be performed by one or more processors or processor-implemented modules.

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities.

Although an overview of the inventive subject matter has been described with reference to specific example embodiments, various modifications and changes may be made to these embodiments without departing from the broader spirit and scope of embodiments of the present invention. For example, various embodiments or features thereof may be mixed and matched or made optional by a person of ordinary skill in the art. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are believed to be described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present invention as represented by the appended claims. The specification and drawings are, accordingly, to be regarded in an illustrative rather than a restrictive sense.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method for detecting and reporting, with a processor, a variant as a repeat of at least two nucleotide patterns in a genomic sequence of a patient sample, the method comprising:

(a) identifying a reference repeat pattern $P_{ref}=N*l$ as the repeat of l (l>=2) genomic patterns N in a genomic region of a human genome reference sequence;

(b) obtaining, with a next generation sequencer, n patient sets of next generation sequencing data reads covering the reference repeat pattern genomic region $S=\{S_1, S_2, \ldots, S_i, \ldots, S_n\}$ from a pool of n enriched genomic patient samples, each set $S_i$ being associated with a patient sample, the number n of enriched genomic patient samples being at least 4, wherein the pool of n enriched genomic patient samples is obtained by aligning and re-aligning the next generation sequencing data reads, via a realignment algorithm executed by a genomic data analyzer, to provide refined data variant calling data comprising the enriched genomic patient samples, wherein aligning and re-aligning the next generation sequencing reads comprises the steps of:

receiving a next generation sequencing analysis request;

identifying, via the genomic data analyzer, a first set of characteristics associated with the next generation sequencing analysis request;

executing, via the genomic data analyzer, a first data alignment; and identifying, from the first data alignment, via the genomic data analyzer, a second set of characteristics including a data alignment pattern identifier, wherein the genomic data analyzer automatically identifies one or more reads with soft clipping regions from the first data alignment, and wherein the genomic data analyzer configures a data alignment module to execute a data re-alignment on the one or more reads with soft clipping regions;

(c) for each patient sample i in the set S of patient samples, measuring the distribution $P_i$ of the length of the repeat pattern in the set of next generation sequencing reads $S_i$, (d) for a possible pair of patient samples i and j, j>i, estimating a best-fit model $$[V_{ij}^1|V_{ij}^2]$$

of the two allele variants for sample i relative to sample j, with a confidence level $L_{ij}$, (e) for each possible triplet of patient samples i, j>i, k>j, comparing their respective best-fit models $$[V_{ij}^1|V_{ij}^2], [V_{jk}^1|V_{jk}^2], [V_{ik}^1|V_{ik}^2],$$

grouping matching best-fit models into groups of best-fit variant models with an increased confidence level, and iterating the comparison until stable groups of best-fit variant models are formed;

(f) identifying the most likely group carrying the wild type variant from the stable groups of best-fit variant models;

(g) for each patient sample in the most likely group carrying the wild type variant, reporting the sample variant as the wild type reference repeat pattern $P_{ref}=N*1$;

(h) for each patient sample out of the most likely group carrying the wild type variant, unbiasing the best-fit variant model of the group comprising this sample as a function of the best-fit variant model for the identified wild type group and reporting the sample variant as the unbiased best-fit model variant to determine whether a patient corresponding with each patient sample out of the most likely group carrying the wild type variant has either a hereditary disease or a somatic disease.

2. The method of claim 1, wherein estimating a best-fit model $$[V_{ij}^1|V_{ij}^2]$$

of the two allele variants for sample i relative to sample j comprises:

(d1) estimating for sample j, under the assumption that sample i carries the wild type human genome reference homopolymer pattern $P_{ref}$ N*1 for each allele, a best-fit model $$[V_{j|i}^1|V_{j|i}^2]$$

of the two allele variants for sample j, with a confidence level $L_{j|i}$, as well as the smallest distance $D_{j|i}$ between the measured distribution $P_j$ for sample j and a predicted unimodal or bimodal distribution for the best-fit variant model $$[V_{j|i}^1|V_{j|i}^2];$$

(d2) estimating for sample i, under the assumption that sample j carries the wild type human genome reference homopolymer pattern $P_{ref}=N*1$ for each allele, a best-fit model $$[V_{i|j}^1|V_{i|j}^2]$$

of the two allele variants for sample i, with a confidence level $L_{i|j}$, as well as the smallest distance $D_{i|j}$ between the measured distribution $P_i$ for sample i and the predicted unimodal or bimodal distribution for the best fit variant model $$[V_{i|j}^1|V_{i|j}^2];$$

(d3) if $D_{i|j} \geq D_{j|i}$, selecting for the pair of samples (i,j) the best-fit model $$[V_{ij}^1|V_{ij}^2] = [-V_{j|i}^1|-V_{j|i}^2]$$

as the best-fit variant model of the two allele variants and the confidence level $L_{ij}=L_{j|i}$ as the confidence level value for this best-fit match with sample i as the reference sample of pair (i,j);

(d4) else if $D_{ij}<D_{j|i}$ selecting for the pair of samples (i,j) the model $$[V_{ij}^1|V_{ij}^2] = [V_{i|j}^1|V_{i|j}^2]$$

as the best-fit variant model of the two allele variants and the confidence level $L_{ij}=L_{i|j}$ as the confidence level value for this best-fit match with sample j as the reference sample of pair (i,j).

3. The method of claim 2, further comprising estimating a secondary best-fit model $$[V_{j|i}^{1'}|V_{j|i}^{2'}]$$

of the two allele variants for sample j, under the assumption that sample i carries the wild type human genome reference homopolymer pattern $P_{ref}=N*1$ for each allele, as well as the second smallest distance $D_{j|i}'$ between the measured distribution $P_j$ for sample j and the predicted unimodal or bimodal distribution for the secondary best-fit variant model $$[V_{j|i}^{1'}|V_{j|i}^{2'}],$$

estimating a secondary best-fit model $$[V_{i|j}^{1'}|V_{i|j}^{2'}]$$

of the two allele variants for sample i, under the assumption that sample j carries the wild type human genome reference homopolymer pattern $P_{ref}$ N*1 for each allele, as well as the second smallest distance $D_{i|j}'$ between the measured distribution $P_i$ for sample i and the predicted unimodal or bimodal distribution for the secondary best-fit variant model $$[V_{j|i}^{1'}|V_{j|i}^{2'}],$$

and calculating the confidence level $L_{ij}$ of the estimation $$[V_{ij}^1 \mid V_{ij}^2]$$

as:

$$L_{ij} = \begin{cases} 1 - D_{i|j}/D_{i|j}', & \text{if } D_{i|j} > D_{j|i} \\ 1 - D_{j|i}/D_{j|i}', & \text{if } D_{i|j} \leq D_{j|i} \end{cases}.$$

4. The method of claim 1, further comprising grouping together into q different groups of samples ($1 \leq q \leq n-1$) based on

37

$$[V^1_{ij,k} \,|\, V^2_{ij,k}]$$

values such that within each group of samples $G_r(1\le r\le q)$, all results agree with each other, and calculating the overall confidence level for this group as $$L_{ij,Gr} = 1 - \prod_{k \in G_r}(1 - L_{ij,k}).$$

5. The method of claim 4, wherein the best-fit models $$[V^1_{ij}|V^2_{ij}]$$

corresponding to different types of heterozygous mutations are excluded from the grouping of matching best-fit models.

6. The method of claim 4, comprising selecting the group $G_h$ with the highest confidence level $L_{ij,Gh}$, setting the value $$[V^1_{ij.Gh}|V^2_{ij.Gh}]$$

of all samples in this group and calculating the new confidence level for pair i,j as $$L_{ij,new} = \max\!\left(0,\, 1 - (1 - L_{ij.Gh}) * \prod_{1\le r\le q, r\ne h}(1 - L_{ij.Gr})^{-1}\right).$$

7. The method of claim 4, further comprising iterating grouping together groups of samples until the results are stable.

8. The method of claim 1, comprising for each possible triplet of patient samples i, j>i, k>j, comparing their respective best-fit models $$[V^1_{ij}|V^2_{ij}],\, [V^1_{jk}|V^2_{jk}],\, [V^1_{ik}|V^2_{ik}]$$

and if all three best-fit models for the triplet of patient samples match each other, increasing their confidence levels $L_{ij}$, $L_{jk}$, $L_{ik}$; else the three best-fit models do not match each other, replacing the best-fit model with the lowest confidence level out of the subset by a best-fit model calculated from the other two samples of the subset, and decreasing the confidence levels $L_{ij}$, $L_{jk}$, $L_{ik}$ of all the best-fit models for the triplet of patient samples, and repeating the comparison for all possible triplets until the results are no longer varying.

9. The method of claim 8 wherein the confidence levels for each pair in a triplet subset i, j, k of matching best-fit models are increased as $L_{ij}'=1-(1-L_{ij})(1-L_{jk}*L_{ik})$, $L_{jk}'=1-(1-L_{jk})(1-L_{ij}*L_{ik})$ and $L_{ik}'=1-(1-L_{ik})(1-L_{ij}*L_{jk})$.

10. The method of claim 8 wherein the lowest initial confidence level is $L_{ik}$ for the pair j,k within the triplet, the confidence levels for each pair in a triplet subset i, j, k of non-matching best-fit models are decreased as $L_{ij}'=L_{ij}(1-L_{jk})*L_{ik}$, $L_{jk}'=L_{jk}(1-L_{ij})*L_{ik}$ and $L_{ik}'=\max(0, L_{ij}*L_{jk}-L_{ik})$ and the best-fit model for the pair j,k with the lowest confidence level out of the subset is replaced by

38

$$[V^{1'}_{ik}|V^{2'}_{ik}] = [V^1_{ij} + V^1_{ij}|V^2_{jk} + V^2_{jk}].$$

11. The method of claim 10, wherein identifying the subset of one or more samples corresponding to the wild type reference in the pool of patient samples consists of selecting as the wild type the homozygous best-fit variant model group $[V_G|V_G]$ with which the largest number of samples i, j, . . . have been associated out of cross-analyzing the pool of samples.

12. The method of claim 10, wherein identifying the subset of one or more samples corresponding to the wild type reference in the pool of patient samples comprises verifying for each group G of homozygous best-fit variant model $$[V^1_G|V^2_G],$$

if $$[V^1_{G'}|V^2_{G'}]$$

is a possible variant for each other group G' of best-fit variant model $$[V^1_{G'}|V^2_{G'}],$$

under the hypothesis that the homozygous best-fit variant model $$[V^1_G|V^2_G]$$

is the wild type, and if that is not the case, excluding group G as carrying the wild type pattern.

13. The method of claim 12, wherein $$V^1_{G'} < V^1_G \text{ and } V^2_{G'} < V^2_G,$$

comprising verifying that the length of the repeat pattern with the $$[V^1_{G'}|V^2_{G'}]$$

best-fit variant model is long enough to be detected as a plausible deletion variant.

14. The method of claim 12, wherein $$V^1_{G'} > V^1_G \text{ and/or } V^2_{G'} > V^2_G,$$

comprising verifying that the length of the repeat pattern with the $$[V^1_{G'} | V^2_{G'}]$$

best-fit variant model is short enough to be detected as a plausible insertion variant.

15. The method of claim 10, further comprising estimating an error rate based on the average homopolymer length $\bar{h}$ and the standard deviation SD for each group of homozygous best-fit variant model $$[V^1_G | V^2_G],$$

and if $\bar{h}$ is within a pre-defined threshold threshold_h to the nearest integer $[\bar{h}]$, that is if abs $(\bar{h}-[\bar{h}])<$threshold_h, and if SD is small enough to be under a predefined threshold threshold_sd, that is if SD<threshold_sd, selecting the homozygous best-fit variant model $$[V^1_G | V^2_G]$$

as the wild type reference with the lowest error rate.

16. The method of claim 15, wherein threshold_h is chosen in the range of 0 to 0.1.

17. The method of claim 15, wherein threshold_sd is chosen in the range of 0 to 0.1.

18. The method of claim 1, wherein aligning and re-aligning the next generation sequencing reads further comprises the steps of:
    refining the aligned sequencing data in accordance with at least one characteristic of the first set of characteristics and at least one characteristic of the second set of characteristics;

identifying a third set of characteristics associated with the refined alignment sequencing data;
detecting a first set of genomic variants associated with the refined alignment sequencing data in accordance with at least one characteristic of the first set of characteristics, at least one characteristic of the second set of characteristics, and at least one characteristic of the third set of characteristics;
identifying a fourth set of characteristics associated with the detected first set of genomic variants;
detecting variants associated with the refined alignment data in accordance with at least one characteristic of the first set of characteristics, at least one characteristic of the second set of characteristics, at least one characteristic of the third set of characteristics and at least one characteristic of the fourth set of characteristics, wherein the pool n of enriched genomic patient samples comprises the variants;
wherein the first set of characteristics includes at least one of:
    a target enrichment technology identifier,
    a sequencing technology identifier, and
    a genomic context identifier;
wherein, during the first data alignment, the genomic data analyzer removes one or more assay specific adapters from the next generation sequencing data reads; and
wherein, the data alignment pattern comprises one or more soft clip patterns.

19. The method of claim 1, wherein the n patient sets of next generation sequencing data reads are sourced from a plurality of next generation sequencing laboratories.

20. The method of claim 1, wherein the next generation sequencer processes n patient sets of next generation sequencing data reads in parallel and generates one or more corresponding sequence reads in a computer-readable file.

*    *    *    *    *